US010568975B2

(12) United States Patent
Yu et al.

(10) Patent No.: US 10,568,975 B2
(45) Date of Patent: Feb. 25, 2020

(54) NANOPARTICLES FOR MAGNETIC RESONANCE IMAGING TRACKING AND METHODS OF MAKING AND USING THEREOF

(71) Applicant: The Johns Hopkins University, Baltimore, MD (US)

(72) Inventors: Tao Yu, Baltimore, MD (US); Himatkumar Patel, Baltimore, MD (US); Kannie M. Y. Chan, Baltimore, MD (US); Nikita Oskolkov, Reisterstown, MD (US); Michael McMahon, Columbia, MD (US); Justin Hanes, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/765,881

(22) PCT Filed: Feb. 5, 2014

(86) PCT No.: PCT/US2014/014872
§ 371 (c)(1),
(2) Date: Aug. 5, 2015

(87) PCT Pub. No.: WO2014/124006
PCT Pub. Date: Aug. 14, 2014

(65) Prior Publication Data
US 2016/0206760 A1 Jul. 21, 2016

Related U.S. Application Data

(60) Provisional application No. 61/760,897, filed on Feb. 5, 2013.

(51) Int. Cl.
*A61K 49/18* (2006.01)
(52) U.S. Cl.
CPC ...... *A61K 49/1878* (2013.01); *A61K 49/1833* (2013.01)
(58) Field of Classification Search
None
See application file for complete search history.

(56) References Cited

U.S. PATENT DOCUMENTS

| | | | |
|---|---|---|---|
| 4,027,676 A | 6/1977 | Mattei |
| 4,201,216 A | 5/1980 | Mattei |
| 4,816,567 A | 3/1989 | Cabilly |
| 4,857,602 A | 8/1989 | Casey |
| 4,994,074 A | 2/1991 | Bezwada |
| 4,997,652 A | 3/1991 | Wong |
| 5,013,556 A | 5/1991 | Woodle |
| 5,019,400 A | 5/1991 | Gombotz |
| 5,034,506 A | 7/1991 | Summerton |
| 5,071,795 A | 12/1991 | Beall |
| 5,091,652 A | 2/1992 | Mathies |
| 5,412,072 A | 5/1995 | Sakurai |
| 5,445,934 A | 8/1995 | Fodor |
| 5,522,842 A | 6/1996 | Shalaby |
| 5,540,930 A | 7/1996 | Guy |
| 5,552,160 A | 9/1996 | Liversidge |
| 5,567,435 A | 10/1996 | Hubbell |
| 5,576,311 A | 11/1996 | Guy |
| 5,578,325 A | 11/1996 | Domb |
| 5,624,821 A | 4/1997 | Winter |
| 5,696,298 A | 12/1997 | Emanuele |
| 5,710,135 A | 1/1998 | Leenders |
| 5,869,130 A | 2/1999 | Ferrier |
| 5,932,462 A | 8/1999 | Harris |
| 6,007,845 A | 12/1999 | Domb |
| 6,194,551 B1 | 2/2001 | Idusogie |
| 6,235,869 B1 | 5/2001 | Roby |
| 6,270,806 B1 | 8/2001 | Liversidge |
| 6,287,588 B1 | 9/2001 | Shih |
| 6,413,539 B1 | 7/2002 | Shalaby |
| 6,432,381 B2 | 8/2002 | Liversidge |
| 6,495,164 B1 | 12/2002 | Ramstack |
| 6,509,323 B1 | 1/2003 | Davis |
| 6,589,549 B2 | 7/2003 | Shih |
| 6,706,289 B2 | 3/2004 | Lewis |
| 7,052,678 B2 | 5/2006 | Vanbever |
| 7,550,154 B2 | 6/2009 | Saltzman |
| 7,638,137 B2 | 12/2009 | Chauhan |
| 7,645,736 B2 | 1/2010 | Bender |
| 7,648,959 B2 | 1/2010 | Bender |

(Continued)

FOREIGN PATENT DOCUMENTS

| | | |
|---|---|---|
| CA | 1072413 | 2/1980 |
| CN | 101797232 | 8/2010 |

(Continued)

OTHER PUBLICATIONS

Arifin et al (Remote MRI Sensing of pH and Cell Viability using Immunoprotective Microcapsules Crosslinked with Polycationic DIACEST Peptides. Proc. Intl. Soc. Mag. Reson. Med. 18 (2010), p. 42).*

(Continued)

*Primary Examiner* — Jake M Vu
(74) *Attorney, Agent, or Firm* — Pabst Patent Group LLP

(57) ABSTRACT

Surface conjugated diamagnetic Chemical Exchange Saturation Transfer (diaCEST) agent carriers and methods of making and using are described herein. The particles are safe alternatives to conventional paramagnetic or superparamagnetic metal-based MRI contrast agents that are often toxic and therefore not biocompatible. The carriers described herein can provide simultaneous monitoring of multiple particle types labeled with 'multicolor' diaCEST contrast agents. In some embodiments, the carriers are micro- and/or nanoparticles. In other embodiments, the carriers are liposomes. In some embodiments, the particles and/or liposomes are mucus penetrating. In other embodiments, the particles and/or liposomes are not mucus penetrating.

27 Claims, 7 Drawing Sheets

Specification includes a Sequence Listing.

(56) References Cited

U.S. PATENT DOCUMENTS

| | | |
|---|---|---|
| 8,056,057 B2 | 11/2011 | Larab |
| 8,071,795 B2 | 12/2011 | VanMeir |
| 8,304,253 B2 | 11/2012 | Yi |
| 8,354,476 B2 | 1/2013 | Hanes |
| 8,394,799 B2 | 3/2013 | Lee |
| 8,409,607 B2 | 4/2013 | Hughes |
| 8,459,295 B2 | 6/2013 | Kim |
| 8,465,778 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,663,674 B2 | 3/2014 | Wen |
| 8,834,695 B2 | 9/2014 | Wang |
| 8,883,014 B2 | 11/2014 | Nelson |
| 8,889,193 B2 | 11/2014 | McDonnell |
| 8,911,768 B2 | 12/2014 | Whitcup |
| 8,957,034 B2 | 2/2015 | Hanes |
| 8,962,577 B2 | 2/2015 | Hanes |
| 9,005,544 B2 | 4/2015 | Van Dam |
| 9,056,057 B2 | 6/2015 | Popov |
| 9,169,573 B2 | 10/2015 | Hadwen |
| 9,341,749 B2 | 5/2016 | Hongo |
| 9,808,800 B2 | 11/2017 | Chen |
| 9,950,072 B2 | 4/2018 | Hanes |
| 1,009,250 A1 | 10/2018 | Maisel |
| 10,092,509 B2 | 10/2018 | Maisel |
| 2002/0035264 A1 | 3/2002 | Kararli |
| 2003/0013880 A1 | 1/2003 | Murthy |
| 2003/0042137 A1 | 3/2003 | Mao |
| 2003/0068277 A1 | 4/2003 | Vanbever |
| 2003/0118550 A1 | 6/2003 | Kabanov |
| 2004/0060977 A1 | 4/2004 | Proennecke |
| 2004/0162580 A1 | 8/2004 | Hain |
| 2004/0209806 A1 | 10/2004 | Rothenberg |
| 2004/0209807 A1 | 10/2004 | Quay |
| 2004/0234611 A1 | 11/2004 | Ahlheim |
| 2004/0258763 A1 | 12/2004 | Bell |
| 2005/0009910 A1 | 1/2005 | Hughes |
| 2005/0059881 A1 | 3/2005 | Balaban |
| 2005/0070448 A1 | 3/2005 | Kupper |
| 2005/0149118 A1 | 7/2005 | Koyfman |
| 2005/0149119 A1 | 7/2005 | Koyfman |
| 2006/0204443 A1 | 9/2006 | Kobayashi |
| 2007/0071756 A1 | 3/2007 | Peyman |
| 2007/0087989 A1 | 4/2007 | Huang |
| 2007/0093461 A1 | 4/2007 | Shafiee |
| 2007/0111959 A1 | 5/2007 | Yockman |
| 2007/0117102 A1 | 5/2007 | Buzby |
| 2007/0141143 A1 | 6/2007 | Smithey |
| 2007/0149593 A1 | 6/2007 | Ghosh |
| 2007/0219122 A1 | 9/2007 | Glazer |
| 2007/0231360 A1 | 10/2007 | Peyman |
| 2007/0238654 A1 | 10/2007 | Deschatelets |
| 2007/0249536 A1 | 10/2007 | Ma |
| 2008/0050920 A1 | 2/2008 | Kawahara |
| 2008/0070920 A1 | 3/2008 | Guo |
| 2008/0086199 A1 | 4/2008 | Dave |
| 2008/0166411 A1 | 7/2008 | Shah |
| 2008/0166414 A1 | 7/2008 | Hanes |
| 2008/0268243 A1 | 10/2008 | Stopek |
| 2008/0287341 A1 | 11/2008 | Chen |
| 2008/0287990 A1 | 11/2008 | Smit |
| 2008/0305172 A1 | 12/2008 | Ahlheim |
| 2009/0011040 A1 | 1/2009 | Naash |
| 2009/0060979 A1 | 3/2009 | Bezwada |
| 2009/0087494 A1 | 4/2009 | Kompella |
| 2009/0138041 A1 | 5/2009 | Stopek |
| 2009/0186771 A1 | 7/2009 | Siddiqi |
| 2009/0196844 A1 | 8/2009 | Choi |
| 2009/0203709 A1 | 8/2009 | Steinberg |
| 2009/0220572 A1 | 9/2009 | Deschatelets |
| 2009/0226531 A1 | 9/2009 | Lyons |
| 2009/0234375 A1 | 9/2009 | Simon |
| 2009/0247604 A1 | 10/2009 | Tang |
| 2009/0291919 A1 | 11/2009 | Kaushal |
| 2010/0034749 A1 | 2/2010 | Schulze |
| 2010/0063135 A1 | 3/2010 | Dande |
| 2010/0094340 A1 | 4/2010 | Stopek |
| 2010/0152831 A1 | 6/2010 | Guo |
| 2010/0166865 A1* | 7/2010 | Kumar ............... A61K 9/5115 |
| | | 424/486 |
| 2010/0208350 A1 | 8/2010 | Yoshihara |
| 2010/0209469 A1 | 8/2010 | Bezwada |
| 2010/0215580 A1 | 8/2010 | Hanes |
| 2010/0227905 A1 | 9/2010 | Kabra |
| 2010/0247669 A1 | 9/2010 | Eliasof |
| 2011/0081647 A1 | 4/2011 | Siddiqi |
| 2011/0163080 A1 | 7/2011 | Beck |
| 2011/0165074 A1* | 7/2011 | Gruell ............... A61K 9/1075 |
| | | 424/1.65 |
| 2011/0262406 A1 | 10/2011 | Campo |
| 2011/0264139 A1 | 10/2011 | Hunter |
| 2012/0028910 A1 | 2/2012 | Combal |
| 2012/0040956 A1 | 2/2012 | Wabnitz |
| 2012/0041481 A1 | 2/2012 | Daniloff |
| 2012/0052041 A1 | 3/2012 | Basu |
| 2012/0121661 A1 | 5/2012 | Schwartz |
| 2012/0157499 A1 | 6/2012 | Hughes |
| 2012/0201873 A1 | 8/2012 | Hohlbaum |
| 2012/0245629 A1 | 9/2012 | Gross |
| 2012/0269894 A1 | 10/2012 | Ahlheim |
| 2012/0288464 A1 | 11/2012 | Carmichael |
| 2012/0303010 A1 | 11/2012 | Vijfvinkel |
| 2013/0041407 A1 | 2/2013 | Montenegro |
| 2013/0071349 A1 | 3/2013 | Robinson |
| 2013/0122064 A1 | 5/2013 | Ahlheim |
| 2013/0130002 A1 | 5/2013 | Lee |
| 2013/0164343 A1 | 6/2013 | Hanes |
| 2013/0164493 A1 | 6/2013 | Hirai |
| 2013/0183244 A1 | 7/2013 | Hanes |
| 2013/0189743 A1 | 7/2013 | Balasubramanian |
| 2013/0217657 A1 | 8/2013 | Lindstrom |
| 2013/0226234 A1 | 8/2013 | Avelar |
| 2013/0236556 A1 | 9/2013 | Lai |
| 2013/0272994 A1 | 10/2013 | Fu |
| 2013/0274217 A1 | 10/2013 | Hanes |
| 2013/0316001 A1 | 11/2013 | Popov |
| 2013/0316006 A1 | 11/2013 | Popov |
| 2013/0316009 A1 | 11/2013 | Popov |
| 2013/0323313 A1 | 12/2013 | Suk |
| 2014/0031408 A1 | 1/2014 | Edelman |
| 2014/0107025 A1 | 4/2014 | Wirostko |
| 2014/0163080 A1 | 6/2014 | Horn |
| 2014/0178475 A1 | 6/2014 | Figueiredo |
| 2014/0212661 A1 | 7/2014 | Khan |
| 2014/0248358 A1 | 9/2014 | Figueiredo |
| 2014/0249158 A1 | 9/2014 | Figueiredo |
| 2014/0271903 A1 | 9/2014 | Sutariya |
| 2014/0276482 A1 | 9/2014 | Astafieva |
| 2014/0294986 A1 | 10/2014 | Liu |
| 2014/0329913 A1 | 11/2014 | Hanes |
| 2015/0044270 A1 | 2/2015 | McDonnell |
| 2015/0086484 A1 | 3/2015 | Hanes |
| 2015/0125539 A1 | 5/2015 | Popov |
| 2015/0265542 A1 | 9/2015 | Popov |
| 2015/0265543 A1 | 9/2015 | Popov |
| 2015/0297531 A1 | 10/2015 | Ensign |
| 2016/0040027 A1 | 2/2016 | Woo |
| 2016/0185926 A1 | 6/2016 | Song |
| 2016/0320803 A1 | 11/2016 | Oh |
| 2017/0012225 A1 | 1/2017 | Heo |
| 2017/0090618 A1 | 3/2017 | Qiao |
| 2017/0106636 A1 | 4/2017 | Jo |
| 2017/0174938 A1 | 6/2017 | Shin |
| 2017/0276840 A1 | 9/2017 | Horio |
| 2017/0324059 A1 | 11/2017 | Choi |

FOREIGN PATENT DOCUMENTS

| | | |
|---|---|---|
| CN | 101926775 | 9/2011 |
| CN | 103833998 | 6/2014 |
| CN | 1038897174 | 7/2014 |

(56) References Cited

FOREIGN PATENT DOCUMENTS

| | | |
|---|---|---|
| EP | 1356809 | 10/2003 |
| EP | 1752142 | 2/2007 |
| EP | 2161020 | 3/2010 |
| EP | 2351556 | 8/2011 |
| KR | 1020110037622 | 4/2011 |
| KR | 101168073 | 7/2012 |
| KR | 1020130055311 | 5/2013 |
| KR | 1020130071941 | 7/2013 |
| KR | 1020140121176 | 10/2014 |
| KR | 101737155 | 4/2015 |
| KR | 1020160079549 | 7/2016 |
| KR | 1020160130074 | 11/2016 |
| KR | 1020170005957 | 1/2017 |
| KR | 1020170043885 | 4/2017 |
| KR | 101748009 | 6/2017 |
| KR | 102017008293 | 8/2017 |
| WO | 9207866 | 5/1992 |
| WO | 94027578 | 12/1994 |
| WO | 9742962 | 11/1997 |
| WO | 98059064 | 12/1998 |
| WO | 9901498 | 1/1999 |
| WO | 9958572 | 11/1999 |
| WO | 0046147 | 8/2000 |
| WO | 0066180 | 11/2000 |
| WO | 0224232 | 3/2002 |
| WO | 2002/038127 | 5/2002 |
| WO | 2006/109177 | 5/2002 |
| WO | 2002038127 | 5/2002 |
| WO | 2006109177 | 5/2002 |
| WO | 02060412 | 8/2002 |
| WO | 2005/012407 | 2/2005 |
| WO | 2005012407 | 2/2005 |
| WO | 2005/055985 | 6/2005 |
| WO | 2005055985 | 6/2005 |
| WO | 2005/072710 | 8/2005 |
| WO | 2005072710 | 8/2005 |
| WO | 2006/005880 | 1/2006 |
| WO | 2006005880 | 1/2006 |
| WO | 2006/063249 | 6/2006 |
| WO | 2006063249 | 6/2006 |
| WO | 2006/116107 | 11/2006 |
| WO | 2006/122542 | 11/2006 |
| WO | 2006114739 | 11/2006 |
| WO | 2006116107 | 11/2006 |
| WO | 2006122542 | 11/2006 |
| WO | 2007/016380 | 2/2007 |
| WO | 2007016380 | 2/2007 |
| WO | 2007/084418 | 7/2007 |
| WO | 2007084418 | 7/2007 |
| WO | 2007/133812 | 11/2007 |
| WO | 2007133812 | 11/2007 |
| WO | 2008/030557 | 3/2008 |
| WO | 2008030557 | 3/2008 |
| WO | 2008/061536 | 5/2008 |
| WO | 2008061536 | 5/2008 |
| WO | 2008117927 | 10/2008 |
| WO | 2009/046446 | 4/2009 |
| WO | 2009/055312 | 4/2009 |
| WO | 2009046446 | 4/2009 |
| WO | 2009055312 | 4/2009 |
| WO | 2009/151539 | 12/2009 |
| WO | 2009151539 | 12/2009 |
| WO | 2010/040188 | 4/2010 |
| WO | 2010040188 | 4/2010 |
| WO | 2010075072 | 7/2010 |
| WO | 2010/086406 | 8/2010 |
| WO | 2010086406 | 8/2010 |
| WO | 2010/132664 | 11/2010 |
| WO | 2010132664 | 11/2010 |
| WO | 2010/143969 | 12/2010 |
| WO | 2010143969 | 12/2010 |
| WO | 2011/080148 | 7/2011 |
| WO | 2011080148 | 7/2011 |
| WO | 2013/102011 | 7/2013 |
| WO | 2013/110027 | 7/2013 |
| WO | 2013/110028 | 7/2013 |
| WO | 2013102011 | 7/2013 |
| WO | 2013110027 | 7/2013 |
| WO | 2013110028 | 7/2013 |
| WO | 2013/138343 | 9/2013 |
| WO | 2013/138346 | 9/2013 |
| WO | 2013138343 | 9/2013 |
| WO | 2013138346 | 9/2013 |
| WO | 2013158719 | 10/2013 |
| WO | 2013/166385 | 11/2013 |
| WO | 2013/166408 | 11/2013 |
| WO | 2013/166436 | 11/2013 |
| WO | 2013/166498 | 11/2013 |
| WO | 2013166385 | 11/2013 |
| WO | 2013166408 | 11/2013 |
| WO | 2013166436 | 11/2013 |
| WO | 2013166498 | 11/2013 |
| WO | 2014/039185 | 3/2014 |
| WO | 2014/039186 | 3/2014 |
| WO | 2014/047439 | 3/2014 |
| WO | 2014039185 | 3/2014 |
| WO | 2014039186 | 3/2014 |
| WO | 2014047439 | 3/2014 |
| WO | 2004/060977 | 7/2014 |
| WO | 2004060977 | 7/2014 |
| WO | 2015/168347 | 11/2015 |
| WO | 2015168347 | 11/2015 |
| WO | 2016/025745 | 4/2016 |
| WO | 2016025745 | 4/2016 |
| WO | 2016/111251 | 7/2016 |
| WO | 2016/118506 | 7/2016 |
| WO | 2016111251 | 7/2016 |
| WO | 2016118506 | 7/2016 |

OTHER PUBLICATIONS

Kemtong et al (Polymeric nanomedicine for cancer MR imaging and drug delivery. Chem. Commun., 2009, 3497-3510).*

Sherry et al (Chemical exchange saturation transfer contrast agents for magnetic resonance imaging. Annu Rev Biomed Eng. 2008;10:391-411).*

Vladimir (Multifunctional nanocarriers. Adv Drug Deliv Rev. Dec. 1, 2006;58(14):1532-55).*

Freichels et al (Sugar-labeled and PEGylated (bio)degradable polymers intended for targeted drug delivery systems. Carbohydrate Polymers. vol. 86, Issue 3, Aug. 30, 2011, pp. 1093-1106).*

Jeong et al (Cellular recognition of paclitaxel-loaded polymeric nanoparticles composed of poly(γ-benzyl l-glutamate) and poly(ethylene glycol) diblock copolymer endcapped with galactose moiety. International Journal of Pharmaceutics. vol. 296, Issues 1-2, May 30, 2005, pp. 151-16).*

Arifin, et al., "Remote MRI sensing of pH and cell viability using immunoprotective microcapsules crosslinked with polycationic DIACEST peptides", Intl Soc Magnetic Resonance in Med., 18:42, Stockholm Apr. 30-May 7, 2010.

Astete and Sabliov, "Synthesis and characterization of PLGA nanoparticles", J. Biomater. Sci. Polymer Ed. 17:247-89 (2006).

Chan, et al., "Development of CEST liposomes for monitoring nanoparticle-based cancer therapies", Proceeding Intl. Soc Magnetic Resonance Med., 21:0422 21\st meeting, Salt Lake City, Apr. 20-26, 2013.

Evbuomwan, et al., "Nanoparticle-based PARACEST agents: the quenching effect of silica nanoparticles on the CEST signal from surface-conjugated chelates", Contrast Media Mol Imaging, 7(1):19-25 (2012).

Hu, et al., "Reaction parameters of targeted gene repair in mammalian cells", Mol. Biotech., 29:197-210 (2005).

Jain, "The manufacturing techniques of various drug loaded biodegradable poly (lactide-co-glycolide) (PLGA) devices", Biomaterials, 21:2475-90 (2000).

Li, et al., "Microencapsulation by solvent evaporation: state of the art for process engineering approaches", Int. J. Pharm. 363:26-39 (2008).

Liu, et al., "In vivo detection of DIACEST contrast agent labeled Liposomes using MRI", Contrast Media Mole Imaging, 4(6):294 (2009).

(56) References Cited

OTHER PUBLICATIONS

Liu, et al., "In vivo multicolor molecular Mr imaging using diamagnetic chemical exchange saturation transfer liposomes", Magnetic Resonance Med., 67(4):1106-13 (2012).
McMahon, et al., "New multicolor polypeptide diamagnetic chemical exchange saturation transfer (DIACEST) contrast agents for MRI", Magnetic Resonance Med., 60(4):803-12 (2008).
Mundargi, et al, "Nano/micro technologies for delivering macromolecular therapeutics using poly(D,L-lactide-co-glycolide) and its derivatives", J. Control. Release 125:193-209 (2008).
Olsen, et al., "Genomic sequence correction by single-stranded DNA oligonucleotides: role of DNA synthesis and chemical modifications of the oligonucleotide ends", J. Gene Med., 7:1534-44 (2005).
Song, et al., Quantitative CEST imaging wirh reduced MT interference using dual-frequency irradiation, Proceedings Intl Soc Magnetic Resonance Med, 20:4190 (2012).
Sterchak,et al., "Uncharged stereoregular-nucleic acid analogs. 1. Synthesis of a cytosine-containing oligomer with carbamate internucleoside linkages", Organic Chem., 52:4202-6, (1987).
Ward, et al., "A new class of contrast agents for MRI based on proton chemical exchange dependent saturation transfer (CEST)", J Magnetic Resonance, 143:79-87 (2000).
Zhang, et al., "Micelles based on biodegradable poly(L-glutamic acid)-b-polylactide with paramagnetic Gd ions chelated to the shell layer as a potential nanoscale MRI-visible delivery system", Biomacromolecules, 9:36-42 (2008).
International Search Report for corresponding PCT application PCT/US2014/014872 dated Jun. 11, 2014.
Aich, et al., "Development of delivery methods for carbohydrate-based drugs; controlled release of biologically-active short chain fatty acid-hexosamine analogs", Glycoconj. J., 27(4):445-59 (2010).
Angal, et al., "A single amino acid substitution abolishes the heterogeneity of chimeric mouse/human (IgG4) antibody", Mol. Immunol, 30(1):105-8 (1993).
Anton, et al., "Enhanced levels of functional HIV-1 co-receptors on human mucosal T cells demonstrated using intestinal biopsy", Aids, 14(2):1761-5 (2000).
Anton, et al., "First phase 1 double-blind, placebo-controlled randomized rectal microbicide trial using UC781 gel with a novel index of ex vivo efficacy", PloS one, 6(9):e23243 (2011).
Anton, et al., "RMP-02/MTN-006: a phase 1 rectal safety, acceptability, pharmacokinetic, and pharmacokinetic study of tenofovir 1% gel compared with oral tenofovir disproxil fumarate", Aids Res, 28(11):1412-21 (2012).
Apgar, et al., "Multiple-particle tracking measurements of heterogeneities in solutions of actin filaments and actin bundles", Biophys. J., 79:1095-1106 (2000).
Beidoe and Mousa, "Current primary open-angle glaucoma treatments and future directions", Clinical Ophthalmol., 6:1699-707 (2012).
Ben-Shabat, S. et al.,PEG-PLA block copolymer as potential drug carrier: preparation and characterization. Macromol. Biosci. 6:1019-1025 (2006).
Benozzi, et al., "Effect of Brimonidine on Rabbit Trabecular Meshwork Hyaluronidase Activity", Investigative Ophthalmology & Visual Science, 41:2268-2272 (2000).
Bernstein, et al., "Functional and cellular responses in a novel rodent model of anterior ischemic optic neuropathy", Invest Opt Visual Sci., 14(10):4153-62 (2003).
Bertschinger, et al., "Disassembly of polyethylenimine-DNA particles in vitro: implications for polyethylenimine-mediated DNA delivery", J Control Release, 116:96-104 (2006).
Beyerle, et al., "PEGylation affects cytotoxicity and cell-compatibility of poly(ethylene imine) for lung application: structure-function relationships", Toxicol. Appl. Pharmacol. 242:146-54 (2010).
Blessing, et al., "Monomolecular collapse of plasmid DNA into stable virus-like particles", PNAS, 95:1427-31 (1998).
Bonacucina, et al., Thermosensitive Self-Assembling Block Copolymers as Drug Delivery Systems, Polymers, 3(2):779-811 (2011).

Cao, et al., "Quantification of the spatial distribution of rectally applied surrogates for microbicide and semen in colon with SPECT and magnetic resonance imagining", Br J Clin. Pharmacol, 74(6):1013-22 (2012).
Chen, et al., "pH and temperature dual-sensitive liposome gel based on novel cleavable mPEG-Hz-CHEMS polymeric vaginal delivery system", Int J Nanomedicine, 7:2621-30 (2012).
Clark and Friend, "Pharmacokinetics and Topical Vaginal Effects of Two Tenofovir Gels in Rabbits", AIDS Res Hum Retroviruses, 28(11):1458-66 (2012).
Cone, et al., "Barrier properties of mucus", Adv Drug Delivery Rev., 61:75-85 (2009).
Cu, et al., "In vivo distribution of surface-modified PLGA nanoparticles following intravaginal delivery", J Cont. Release, 156(2):257-64 (2011).
Cynkowska, et al., "Novel antiglaucoma prodrugs and codrugs of ethacrynic acid", Bioorganic & Medical Chemistry Letters, 15(15):3524-3527 (2005).
Das Neves et al., "Gels as vaginal drug delivery systems", Int J Pharm., 318(1-2):1-14 (2006).
Date, et al., "Development and evaluation of a thermosensitive vaginal gel containing raltegravir + efavirenz loaded nanoparticles for HIV prophylaxis,", Antiviral Res., 96:430 (2012).
Dauty, et al., "Dimerizable cationic detergents with a low cmc condense plasmid DNA into nanometric particles and transfect cells in culture", J. Am. Chem. Soc. 123:9227-34 (2001).
De Kozak, et al., "Intraocular injection of tamoxifen-loaded nanoparticles: a new treatment of experimental autoimmune uveoretinitis", Eur. J Immunol., 34:3702-12 (2004).
Den, et al., Efficacy of early systemic betamethasone or cyclosporin A after corneal alkali injury via inflammatory cytokine reduction, Acta Ophthalmologica Scandinavica 82(2):195-199 (2004).
Deosarkar, et al.., "Polymeric particles conjugated with a ligand to VCAM-1 exhibit selective, avid, and focal adhesion to sites of atherosclerosis", Biotech. Bioeng., 101(2):400-7 (2008).
Desai, "Pluronic F127-based ocular delivery system containing biodegradable polyisobutylcyanoacrylate nanocapsules of pilocarpine", Drug Delivery, 7:201-7 (2000).
Desai, et al., "Localization of Herpes Simplex Virus Type 1 UL37 in the Golgi Complex Requires UL36 but Not Capsid Structures", J Virology, 82(22):11354-61 (2008).
Dezzutti, et al., "Reformulated tenofovir gel for use as a dural compartment microbicide", J antimicrobial chemotherapythea, 67(9):2139-42 (2012).
Dong, et al., "Vascular cell-adhesion molecule-1 plays a central role in the proangiogenic effects of oxidative stress", PNAS, 108(35):14614-9 (2011).
Donnell, et al., "HIV protective efficacy and correlates of tenofovir blood concentrations in a clinical trial of PrEP for HIV prevention", J Aquir Defic Syndr., 66(3):340-8 (2014).
Donshik, et al., Effect of topical corticosteroids on ulceration in alkali-burned corneas, Archives of Ophthalmology 96(11): 2117-2120 (1978).
Dumortier, et al., "A review of poloxamer 407 pharmaceutical and pharmacological characteristics", Pharm Res., 23(12):2709-28 (2006).
Dunmire and Katz, "Alteration of human sperm kinematics in cervical mucus due to nonoxynol-9", Contraception, 55:209-17 (1997).
Duvall, et al., "Phase 2: a dose-escalation study of OncoGel (ReGel/paclitaxel), a controlled-releaseformulation of paclitaxel, as adjunctive local therapy to external-beam radiation in patients with inoperable esophageal cancer", Anticancer Drugs, 20(2):89-95 (2009).
Eisenberg, et al., "Bimatoprost and travoprost: a review of recent studies of two new glaucoma drugs", Surv. Ophthalmol., 47:S105-15 (2002).
Ensign-Hodges, "Mucus-Penetrating Nanoparticles for Vaginal and Gastrointestinal Drug Delivery", dissertation, Johns Hopkins University (2012).
Ensign, et al., "Enhanced vaginal drug delivery through the use of hypotomic formulations that induce fluid uptake", Biomaterials, 34(28):6922-9 (2013a).

(56) References Cited

OTHER PUBLICATIONS

Ensign, et al., "Ex vivo characterization of particle transport in mucus secretions coating freshly excised mucosal tissues", Mol Pharm, 10(6):2176-82 (2013b).
Ensign, et al., "Mucus Penetrating Nanoparticles: Biophysical Tool and Method of Drug and Gene Delivery", Adv Mater. 24(28):3887-94 (2012b).
Ensign, et at., "Mucus-penetrating nanoparticles for vaginal drug delivery protect against herpes simplex virus", Sci Transl Med., 4(138):138ra79 (2012a).
Epstein, et al., "Influence of ethacrynic acid on outflow facility in the monkey and calf eye", IOVS. 28:2067-75 (1987).
Epstein, et al., "Thiol adducts of ethacrynic acid increase outflow facility in enucleated calf eyes", Curr. Eye Res., 11:253-8 (1992) Abstract Only.
Erdmann and Uhrich, "Synthesis and degradation characteristics of salicylic acid-derived poly(anhydride-esters)", Biomaterials, 21:1941-6 (2000).
Erickson-Lamy, et al., "Ethacrynic acid induces reversible shape and cytoskeletal changes in cultured cells", IOVS, 33:2631-40 (1992).
Escobar-Chavez, "Application of thermo-reversible pluronic F-127 gels in pharmaceutical formulations", J Pharma Sci., 9(3):339-58 (2006).
Extended European Search Report for Application No. 18204801.7 dated May 6, 2019.
Eyles, et al., "The transfer of polystyrene microspheres from the gastrointestinal tract to the circulation after oral administration in the rat", J Pharm Pharmacol., 47:561-5 (1995).
Ferrari, et al., "Barriers to and new approaches for gene therapy and gene delivery in cystic fibrosis", Adv. Drug Deliv. Rev. 54:1373-93 (2002).
Ferrari, et al., "Immunological hurdles to lung gene therapy", Clin. Exp. Immunol., 132:1-8 (2003).
Ferrari, et al., "Polyethylenimine shows properties of interest for cystic fibrosis gene therapy", Biochemica Biophysica Acta., 1447(2-3):219-25 (1999).
Fiegel, et al., "Poly(ether-anhydride) dry powder aerosols for sustained drug delivery in the lungs", J Control Release, 96:411-23 (2004).
Fischer, et al., "A novel non-viral vector for DNA delivery based on low molecular weight, branched polyethylenimine: effect of molecular weight on transfection efficiency and cytotoxicity", Pharm. Res. 16:1273-9 (1999).
Flotte, et al., "Gene therapy in cystic fibrosis", CHEST, 120(3 suppl) 124S-131S (2001).
Fuchs, et al., "Hyperosmolar sexual lubricant causes epithelial damage in the distal colon: potential implication for HIV transmission", J Infect Dis, 195:703-710 (2007).
Fuchs, et al., "Quantitative assessment of altered rectal mucosal permeability due to rectally applied nonoxynol-9, biopsy, and simulated intercourse", J Infect Diseases, 207(9):1389-96 (2013).
Galea, et al., "Rectal douching and implications for rectal microbicides among populations vulnerable to HIV in South America: a qualitative study", Sexually Transmitted Infections, 90(1):33-5 (2014).
Garripelli, et al., "Drug Release from a pH-Sensitive Multiblock Co-Polymer Thermogel", J Biomater Sci Polym Ed, 23(12):1505-19 (2011).
Giannavola, et al., "Influence of preparation conditions on Acyclovir-loaded poly-d, I-lactic acid nanospheres and effect of PEG coating on ocular drug bioavailability", Pharma. Res., 20(4):584-90 (2003).
Gibson, et al., "Recent advances in topical therapeutics for vitreoretinal diseases", US Ophthalmic Review, 8(1): 2-7 (2015).
Giovagnoli, et al., "Formulation and release behavior of doxycycline-alginate hydrogel microparticles embedded into pluronic F127 thermogels as a potential new vehicle for doxycycline intradermal sustained delivery", AAPS PharmSciTech, 11(1):212-20 (2010).
Gou, et al., "Synthesis, self-assembly, and drug-loading capacity of well-defined cyclodextrin-centered drug-conjugated amphiphilic A 14 B 7 miktoarm star copolymers based on poly([epsilon]-caprolactone) and Poly(ethylene glycol)", Biomacromolecules, 11(4):934-43 (2010).
Govender, et al., "PLGA nanoparticles prepared by nanoprecipitation: drug loading and release studies of a water soluble drug", J Cont. Rel., 57:171-85 (1999).
Gref, et al., "'Stealth' corona-core nanoparticles surface modified by polyethylene glycol (PEG): influences of the corona (PEG chain length and surface density) and of the core composition on phagocytic uptake and plasma protein adsorption", Colloids Surf Biointerfaces, 18:301-13 (2000).
Gregory, et al., "Expression and characterization of the cystic fibrosis transmembrane conductance regulator", Nature, 347:382-6 (1990).
Griesenbach and Alton, "Gene transfer to the lung: lessons learned from more than 2 decades of CF gene therapy", Adv. Drug Deliv. Rev. 61:128-39 (2009).
Grinstaff, "Designing hydrogel adhesives for corneal wound repair", Biomaterials, 28(35):5205-14 (2007).
Grinstaff, et al., "Biodendrimers: new polymeric biomaterials for tissue engineering", Chemistry—A European Journal, 8(13):2838-46 (2002). Abstract.
Grisanti and Ziemssen, "Bevacizumab: Off-label uses in ophthalmology", Indian J Ophthalmol., 55(6):417-20 (2007).
Gurwitz, et al., "Treatment for glaucoma: adherence by the elderly", Am. J. Pub. Health, 83:711-6 (1993).
Hendrix, et al., "MTN-001 randomized pharmacokinetic cross-over study comparing tenofovir vaginal-gel and oral tablets in vaginal tissue and other compartments", PloS one, 8(1):e55012 (2013).
Hida, et al., "Common gene therapy viral vectors do not efficiently penetrate sputum from cystic fibrosis patients", PLoS ONE. 6:e19919 (2011).
International Search Report for corresponding PCT application PCT/US2016/013914 dated Apr. 14, 2016.
International Search Report for corresponding PCT application PCT/US2017/014956 dated Apr. 22, 2016.
International Search Report for PCT applicaiton PCT/US2017/016953 dated May 25, 2017.
International Search Report for PCT application PCT/US2015/017120 dated May 29, 2015.
Iwase, et al., "Safe and effective polymeric-doxorubicin conjugate nanoparticles for prolonged antiagiogenic activity in the eye", Retrieved from the internet:URL:http://www.abstractsonline.com/Plan/ViewAbstract.aspx?mID=2866&sKey=ebc9c74c-9d11-43d0-9d5c-060396c9ca9a&cKey=33638dc5-1717-4e08-8287-5344c389580c&mKey-{FOFCE029-9BF8-4E7C-B48E-9FF7711D4A0E}, Accessed May 17, 2013. (abstract).
Jain and Kumar, "Self assembly of amphiphilic (PEG)(3)-PLA copolymer as polymersomes: preparation, characterization, and their evaluation as drug carrier", Biomacromaolecules, 11:1027-35 (2010).
Jain, "The manufacturing techniques of various drug loaded biodegradable poly(lactide-co-glycolide) (PLGA) devices", Biomaterials, 21(23):2475-90 (2000).
Kafedjiiski, et al., "Synthesis and in vitro evaluation of thiolated hyaluronic acid for mucoadhesive drug delivery", Int J Pharm, 343(1-2):48-58 (2007).
Kambhampati, et al., "Intracellular delivery of dendrimer triamcinolone acetonide conjugates into microglial and human retinal pigment epithelial cells", Eur J Pharm Biopharm, Sep95(Pt B):239-49 (2015).
Kaufman and Rasmussen, "Advances in glaucoma treatment and management: outflow drugs", IOVS, 53:2495-2500 (2012).
Kemtong, et al., "Nanoparticles for magnetic resonance imaging tracking and methods of making and using thereof", Chem. Communication, 3497-3510 (2009b).
Kent, "Glaucoma drugs: The search for new options", 8 pages, https://www.reviewofophthalmology.com/article/glaucoma-drugs-the-search-for-new-options Mar. 16, 2007.
Kim, et al., "A thermosensitive vaginal gel formulation with HPgammaCD for the pH-dependent release andsolubilzation of amphotericin B", Eur J Pharm Sci, 2010. 41(2):399-406 (2010).

(56) References Cited

OTHER PUBLICATIONS

Kompella, et al., "Luteinizing hormone-releasing hormone agonist and transferrin functionalizations enhance nanoparticle delivery in a novel bovine ex vivo eye model", Mol. Vis.,12:1185-98 (2006).
Korhonen, et al., "Synthesis of Poly(ester-anhydrides) Based on Different Polyester Precursors", Macromol. Chem. Phys., 205:937-945 (2004).
Lacey, et al., "Unacceptable side-effects associated with a hyperosmolar vaginal microbicide in a phase 1 trial", Int J STD AIDS, 21:714-7 (2007).
Lai, et al., "Mucus-penetrating nanoparticles for drug and gene delivery to mucosal tissues", Adv Drug Deliver Rev., 61:158-71 (2009).
Lai, et al., "Rapid transport of large polymeric nanoparticles in fresh undiluted human mucus", PNAS, 104:1482-7 (2007).
Larkin, et al., "Identification and characterization of cells infiltrating the graft and aqueous humour in rat corneal allograft rejection", Clin. Exp. Immunol., 107:381-91 (1997).
Lavik, et al., "Novel drug delivery systems for glaucoma", Eye, 25:578-86 (2011).
Lemoine, et al., "Mechanism of efficient transfection of the nasal airway epithelium by hypotonic shock", Gene Ther., 12(16):1275-85 (2005).
Lennernas, "Does fluid flow across the intestinal mucosa affect quantitative oral drug absorption? Is it time for a reevaluation?", Pharm Res., 12:1573-82 (1995).
Lesniak, et al., "Biodistribution of fluorescently labeled PAMAM dendrimers in neonatal rabbits: effect of neuroinflammation", Mol Pharma,10:4560-71 (2013).
Levkovitch-Verbin, "Animal models of optic nerve diseases", Eye, 18:1066-74 (2014).
Leyva, et al., "Isoosmolar enemas demonstrate preferential gastrointestinal distribution, safety, and acceptability compared with hyperosmolar enemas and hypoosmolar enemas as a potential delivery vehicle for rectal microbicides", Aids Res., 29(11):1487-95 (2013).
Li, et al., "A long-acting formulation of a polypeptide drug exenatide in treatment of diabetes using an injectable block copolymer hydrogel", Biomaterials, 34(11):2834-42 (2013).
Liang, et al., "Ethacrynic acid increases facility of outflow in the human eye in vitro". Arch. Ophthalmol. 110:106-9 (1992).
Lisco, "Acyclovir Is Activated Into a HIV-1 Reverse Transcriptase Inhibitor in Herpesvirus-Infected Human Tissues", Cell Host & Microbe, 4:260 (2008).
Loh, et al., "Sustained delivery of paclitaxel using thermogelling poly(PEG/PPG/PCL urethane)s for enhanced toxicity against cancer cells", J Biomed Mater Res A., 100(10): 2686-94 (2012).
Louissaint, et al., "Distribution of cell-free and cell-associated HIV surrogates in female genital tract after simulated vaginal intercourse", J Infect Diseases, 205(5):725-32 (2012).
Louissaint, et al., "Distribution of cell-free and cell-associated HIV surrogates in the colon after simulated receptive anal intercourse in men who have sex with men", Acquir Immune Defic Syndr., 59(1):10-17 (2012b).
Louissaint, et al., "Single dose pharmacokinetics of oral tenofovir plasma, peripheral blood mononuclear cells colonic tissue and virginal tissue", Aids Res., 29(11):1443-50 (2013).
Ludwig, "The use of mucoadhesive polymers in ocular drug delivery", Advanced Drug Delivery Reviews 57:1595-1639 (2005).
Macha, et al., "Overview of ocular drug delivery", Ophthalmic Drug Delivery Systems, Second Edition, 1-12 (2003).
Mahajan, "Development and evaluation of gel-forming ocular films based on xyloglucan", Carbohydr Polym, 20:122:243-7 (2015).
Marquis and Whitson, "Management of glaucoma: Focus on pharmacological therapy", Drugs Aging, 22:1-21 (2005).
Mayer, et al., "Safety and tolerability of tenofovir vaginal gel in abstinent and sexually active HIV-infected and uninfected women", Aids, 20(4):543-51 (2006).
McGowan, et al., "A phase 1 randomized double blind placebo controlled rectal safety and acceptability study of tenofovir 1% gel (MTN-007)",PloS one, 8(4):e60147 (2013).
McGowan, et al., Characterization of baseline intestinal mucosal indices of injury and inflammation in men for use in rectal microbicide trials (HIV prevention trials Network-056) Acquir Immune Defic Syndr., 46(4):417-25 (2007).
McGowan, et al., "Charm-01 a Phase 1 rectal safety acceptability PK/PD study of three tenofovir gels",22nd conference on Retroviruses and opportunistic Infections. Seattle Washington (2015).
Meisel, et al. "Human rectal mucos: proctoscopic and morphological changes caused by laxatives", Gastroenterology, 72(6):1274-9 (1977).
Melamed, et al., "The effect of intracamerally injected ethacrynic acid on intraocular pressure in patients with glaucoma", Am. J. Ophthal., 113:508-12 (1992).
Memon, et al., "Optimization of formulation parameters on ocular loteprednol etabonate nanosuspension by media milling method", Int J Pharmacrut. Biol. Arch., 4:46-51 (2012).
Miyazaki, et al., "Thermo-sensitive sol-gel transition of Pluronic F-127", Yakuzaigaku, 51:36-43 (1991).
Moench, et al., "Microbicide excipients can greatly increase susceptibility to genital herpes transmission in the mouse", BMC Infect Dis., 10:331 (2010).
Na, et al., "Menadione and ethacrynic acid inhibit the hypoxia-inducible factor (HIF) pathway by disrupting HIF-1$\alpha$ interaction with p300", Biochem Biophysol Res Comm., 434:879-84 (2013).
Nance, et al., "Nanoscale effects in dendrimer-mediated targeting of neuroinflammation", Biomaterials 101 (2016) 96-107.
Nance, et al., "A dense poly(ethylene glycol) coating improves penetration of large polymeric nanoparticles within brain tissue", Sci Transl Med., 4(149):149ra 119 (2012).
Ndesendo. et al., "A Review of Current Intravaginal Drug Delivery Approaches Employed for the Prophylaxis of HIV/AIDS and Prevention of Sexually Transmitted Infections", AAPS Pharm Sci Tech, 9(2)505-20 (2008).
Newman, et al., "Uptake of poly(D,L-lactic-co-glycolic acid) microspheres by antigen-presenting cells in vivo", J Biomed Mater Res., 60(3):480-6 (2002).
Noach, et al., "Effect of anisotonic conditions on the transport of hydrophilic model compounds across monolayers of human colonic cell lines", J Pharmacol Exp Ther., 270:1373-80 (1994).
Nuttail, et al., "Pharmacokinetics of tenofovir following intravaginal and intrarectal administration of tenofovir gel to rhesus macaques", Antimicrobial agents Chemo., 56(1):103-9 (2012).
Okamoto, et. al., Transgenic mice with increased expression of vascular endothelial growth factor in the retina: a new model of intraretinal and subretinal neovascularization, Am. J. Pathol. 151:281-291 (1997).
Owen, et al., "Factors influencing nonoxynol-9 permeation and bioactivity in cervical mucus", J Control Release, 60:23-34 (1999).
Pandit and Wang, "Salt effects on the diffusion and release rate of propranolol from poloxamer 407 gels", Intl J Pharma., 167(1-2):183-9 (1998).
Park, et al., "Biodegradable thermogels", Acc Chem Res, 45(3):424-33 (2012).
Partial European Search Report for Application No. 18204801.7 dated Jan. 17, 2019.
Patterson, et al., "Penetration of tenofovir and emtricitabane in mucosal tissues: implication for prevention of HIV-! Transmission", Sci Transal Med.,3(112):112re4 (2011).
Perry, et al., "Latanoprost: an update of its use in glaucoma and ocular hypertension", Drugs Aging, 20:597-630 (2003).
Petersen, et al., "High-throughput analysis of protein stability in polyanhydride nanoparticles", Acta Biomateral.. 6:3873-81 (2010).
Phillips, et al., Lubricants containing N-9 may enhance rectal transmission of HIV and other STIs, Contraception, 70(2):107-10 (2004).
Pihl, et al., Comparative study of the effect of luminal hypotonicity on mucosal permeability in rat upper gastrointestinal tract, Acta Physiol., 193:67-78 (2008).
Rao, et al., "For the acylation of hydroxy- and mercapto-carboxylic acid esters by the carbodiimide / acylation catalyst method", Archiv der Pharmazie, 322(9):523-30 (1989). (English Abstract).

(56) References Cited

OTHER PUBLICATIONS

Rajapaksa, et al., "Intranasal M cell uptake of nanoparticles is independently influenced by targeting ligands and buffer ionic strength", J Biol Chem., 285:23739-46 (2010).

Richardson-Harman, et al., Correlation between compartmental tenofovir concentrations and an Ex vivo rectal biopsy model of tissue inflexibility in the RMP-02/MTN-006 Phase !, PloS one, 9(10):e11507 (2014).

Robinson, et al., "Isotretinoin for low-grade cervical dysplasia in human immunodeficiency virus-infected women", Obstet Gynecol, 99:777-84 (2002).

Rudolph, et al., "Aerosolized nanogram quantities of plasmid DNA mediate highly efficient gene delivery to mouse airway epithelium", Mol Ther., 12:493-501 (2005).

Sagong, et al., "Intravitreal becacizumab for the treatment of neovascular glaucoma associated with central retinal artery occlusion", Korean J Ophthalmol., 23:215-8 (2009).

Sahib, et al., "Solubilization of beclomethasone dipropionate in sterically stabilized phospholipid nanomicelles (SSMs):physicochemical and in vitro evaluations", Drug Des Dev Ther., 6:29-42 (2012).

Saishin, et al., "VEGF-TRAP(R1R2) suppresses choroidal neovascularization and VEGF-induced breakdown of the blood-retinal barrier", J. Cell Physiol., 195:241-8 (2003).

Schuman, "Antiglaucoma medications: A review of safety and tolerability issues related to their use", Clin. Therapeut., 22:167-208 (2000).

Segarra, et al., "Bridging the Gap between Preclinical and Clinical Microbicide Trials: Blind Evaluation of Candidate Gels in Murine Models of Efficacy and Safety", Plos One, 6(11):E27675 (2011).

Sheng, et al., "In vitro macrophage uptake and in vivo biodistribution of PLA-PEG nanoparticles loaded with hemoglobin as blood substitutes: effect of PEG content", J Mater Sci Mater Med., 20(9):1881-91 (2009).

Singh, et al., "Cationic microparticles: A potent delivery system for DNA vaccines", PNAS, 98(2):811-6 (2000).

Smith, et al., Oxygen-induced retinopathy in the mouse, Invest. Ophthalmol. Vis. Sci. 35:101-111 (1994).

Sobczak, et al., "Synthesis and characterization of polyester conjugates of ciprofloxacin", Eu. J. Med Chem., 45(9):3844-9 (2010).

Sonis, et al., "Perspectives on Cancer Therapy-Induced Mucosal Injury", Mucositis: Perspectives and Clinical Practice Guidelines, Cancer, Suppl100(9):1995-2025 (2004).

Soppimath, et al., "Biodegradable polymeric nanoparticles as drug delivery devise", J Cont. Release, 70:1-20 (2001).

Stonecipher, et al., "Infectious endophthalmitis following sutureless cataract surgery", Arch Ophthalmol., 109(11):1562-1563 (1991).

Sudol, et al., "Relative safety of sexual lubricants for rectal intercourse", Sexually trans diseases, 31(6):346-9 (2004).

Suh, et al., "PEGylation nanoparticles improves their cytoplasmic transport", Int. J Nanomed., 2(4):735-41 (2007).

Tanaka, et al., "Development of cell-penetrating peptide-modified MPEG-PCL diblock copolymeric nanoparticles for systemic gene delivery", Intl J Pharmac., 396(1-2):229-38 (2010).

Tang, et al., "Enhanced efficacy of local etoposide delivery by poly(ether-anhydride)particles against small cell lung cancer in vivo", Biomaterials, 31:339-44 (2010).

Thigpen, et al., "The role of chemotherapy in the management of carcinoma of the cervix", Cancer J. 9:245-432 (2003).

Tingey, et al., "The effect of intracameral ethacrynic acid on the intraocular pressure of living monkeys", Am. J. Ophthalmol., 113:706-11 (1992).

Tobe, et al., "Targeted disruption of the FGF2 gene does not prevent choroidal neovascularization in a murine model", Am. J. Pathol. 153:1641-1646 (1998).

Ventuneac, et al., "Acceptability of UC781 gel as a rectal microbicide among HIV-uninfected women and men", Aids Behav., 14(3):618-28 (2010).

Veronese, et al., "PEG-doxorubicin conjugates: influence of polymer structure on drug release, in vitro cytotoxicity, biodistribution, and antitumor activity", Bioconjig Chem.,16(4):775-84 (2005).

Wagoner, "Chemical injuries of the eye: current concepts in pathophysiology and therapy", Survey of ophthalmology 41(4):275-313 (1997).

Wang , et al., "Addressing the PEG mucoadhesivity paradox to engineer nanoparticles that "slip" through the human mucus barrier", Angew Chem Int Ed Engl., 47(50):9726-9 (2008).

Wang, et al., "Controlled release of ethacrynic acid from poly(lactide-co-glycolide) films for glaucoma treatment", Biomaterials, 25:4279-85 (2004).

Wang, et al., "Development of in situ gelling and bio adhesive 5-Fluorourocil enema", PLoS One, 2013. 8(8): p. e71037 (2013).

Wang, et al., "Effects of topical ethacrynic acid ointment vs timolol on intraocular pressure in glaucomatous monkey eyes", Arch. Ophthalmol., 112:390-4 (1994).

Wilson, et al., "Epithelial migration in the colon: filling in the gaps", Clin Sci., 93(2):97-108 (1997).

Woodward and Gil, "The inflow and outflow of anti-glaucoma drugs", Trends Pharmacol. Sci. 25:238-41 (2004).

Xu, et al., "Ethacrynic acid inhibition of microtubule assembly in vitro", Arch. Biochem. Biophys. 296:462-7 (1992).

Yang, et al., "A multi-compartment single and multiple dose pharmacokinetic comparison of recently applied tenofovir 1% gel and oral tenofocir disoproxil fumarate". PloS one, 9(10:e106196 (2014).

Yang, et al., "Biodegradable nanoparticles composed entirely of safe materials that Rapidly penetrate human mucus", Agnew. Chem. Int. Ed., 50:1-5 (2011).

Yang, et al., "Production of virus-mimetic mucus-penetrating particles for drug and gene delivery in mucosal tissues", Annual Meeting of AICHE Science and Engineering Forum, Nov. 16-21, Abstract 705B (2008).

Yeon, et al., "3D culture of adipose-tissue-derived stem cells mainly leads to chondrogenesis in poly(ethylene glycol)-poly(L-alanine) diblock copolymer thermogel", Biomacromolecules, 14(9):3256-66 (2013).

Yokoyama, et al., "Characterization and anticancer activity of the micelle-forming polymeric anticancer drug adriamycin-conjugated poly(ethylene glycol)-poly(aspartic acid) block copolymer", Cancer Res., 50:1693-1700 (1990).

Yoshida, et al., Digoxin inhibits retinal ischemia-induced HIF-1alpha expression and ocular neovascularization, Faseb J. 24:1759-1767 (2010.

Yu, et al., "In vitro and in vivo evaluation of a once-weekly formulation of an antidiabetic peptide drug exenatide in an injectable thermogel", J Pharm Sci, 102(11):4140-9 (2013).

Zeitlin, et al., "Tests of Vaginal Microbicides in the Mouse Genital Herpes Model", Contraception, 56:329-335 (1997).

Zhang, et al., ,, "ph-responsive nanoparticles releasing tenofovir intended for the prevention of HIV transmission", Eu J Pharma Biopharma., 79(3):526-36 (2011).

Zhu, et al., "Expression of adhesion molecule CD44 on human corneas", Br J Ophthalmol., 81(1):80-4 (1997).

Giannavola, et al., "Influence of preparation conditions on Acyclovir-loaded poly-d, 1-lactic acid nanospheres and effect of PEG coating on ocular drug bioavailability", *Pharma. Res.*, 20(4):584-90 (2003).

Iwase, et al., "Safe and effective polymeric-doxorubicin conjugate nanoparticles for prolonged antiangiogenic activity in the eye", Retrieved from the internet: URL:http://www.abstractsonline.com/Plan/ViewAbstract.aspx?mID=2866&sKey=ebc9c74c-9d11-43d0-9d5c-060396c9ca9a&cKey=33638dc5-1717-4e08-8287-5344c389580c&mKey-{FOFCE029-9BF8-4E7C-B48E-9FF7711D4A0E}, Accessed May 17, 2013. (Abstract).

Jain and Kumar, "Self-assembly of amphiphilic (PEG) (3)-PLA copolymer as polymersomes: preparation, characterization, and their evaluation as drug carrier", *Biomacromolecules*, 11:1027-35 (2010).

Kim, et al., "A thermosensitive vaginal gel formulation with HPgammaCD for the pH-dependent release and solubilzation of amphotericin B", *Eur J Pharm Sci*, 41(2):399-406 (2010).

Lai, et al., "Mucus-penetrating nanoparticles for drug and gene delivery to mucosal tissues", *Adv. Drug Delivery Rev.*, 61:158-71 (2009).

(56) References Cited

OTHER PUBLICATIONS

Nance, et al., "Nanoscale effects in dendrimer-mediated targeting of neuroinflammation", *Biomaterials*, 101: 96-107 (2016).
Patterson, et al., "Penetration of tenofovir and emtricitabane in mucosal tissues: implication for prevention of HIV Transmission", *Sci. Transl. Med.*, 3(112):112re4 (2011).
Schuman, "Antiglaucoma medications: A review of safety and tolerability issues related to their use", *Clin. Therapeutic.* 22:167-208 (2000).
Sobczak, et al., "Synthesis and characterization of polyester conjugates of ciprofloxacin", *Eur. J. Med Chem.*, 45(9):3844-9 (2010).
Zhang, et al., "ph-responsive nanoparticles releasing tenofovir intended for the prevention of HIV transmission", *Eur. J. Pharma. Biopharma.* 79(3):526-36 (2011).
International Search Report for PCT application PCT/US2017/016953 dated May 25, 2017.

\* cited by examiner

● 0.6 kDA PEG   ○ 5.6 kDA PEG

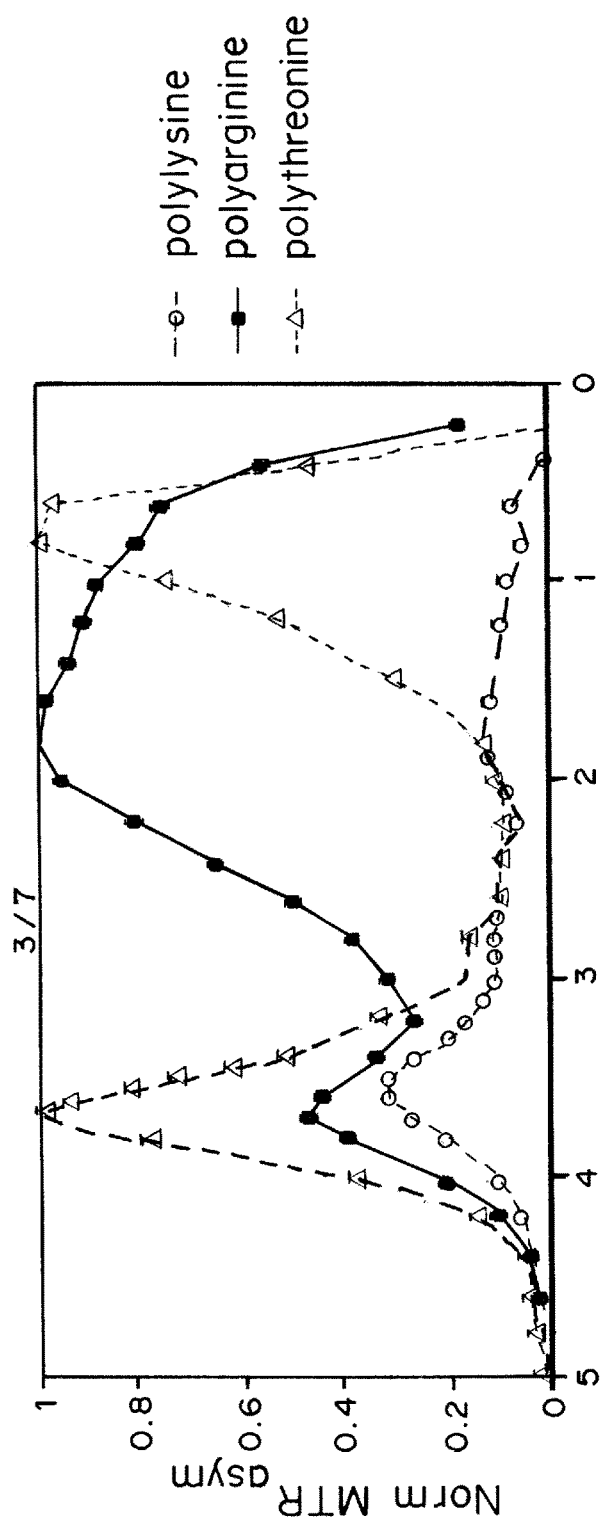
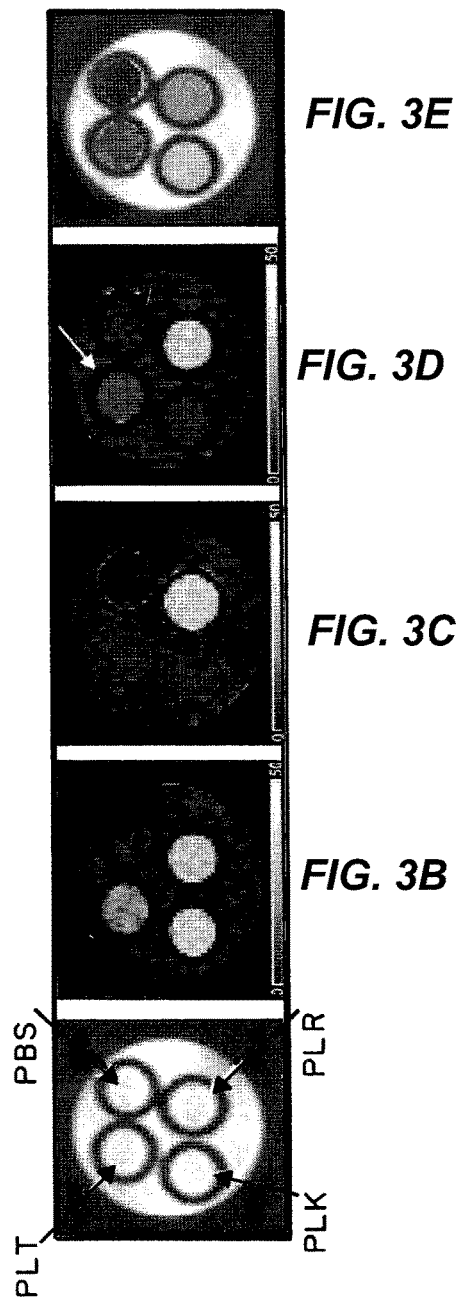
FIG. 3E
FIG. 3D
FIG. 3C
FIG. 3B
FIG. 3A

• 0.6 kDA PEG     ○ 5.6 kDA PEG

NANOPARTICLES FOR MAGNETIC RESONANCE IMAGING TRACKING AND METHODS OF MAKING AND USING THEREOF

CROSS-REFERENCE TO RELATED APPLICATIONS

This application is a 371 application of International Application No. PCT/US2014/014872, filed Feb. 5, 2014, which claims priority to U.S. Ser. No. 61/760,897 entitled "A Surface Conjugated Diamagnetic Chemical Exchange Saturation Transfer Nanoparticle and/or Nanocarrier for Magnetic Resonance Imaging (MRI) Tracking and Methods Therefor", filed on Feb. 5, 2013. The contents of this application are incorporated herein by reference in their entirety.

STATEMENT REGARDING FEDERALLY SPONSORED

This invention was made with government support under grant number EB015031 awarded by the National Institutes of Health. The government has certain rights in the invention.

FIELD OF THE INVENTION

This invention is in the field of nanocarriers for magnetic resonance imaging (MRI) tracking and methods of making and using thereof.

BACKGROUND OF THE INVENTION

In recent years there has been growing interest in the use of nanoparticles for drug delivery. While these nanocarriers have been shown to improve the efficacy of chemotherapy, there have been significant challenges. In cancer therapy, for example, the balance between minimizing exposure of therapeutics to healthy tissues and concurrently target a high dose of chemotherapeutics to tumors and metastases are obstacles that have been difficult to overcome. As nanotherapeutics advance to clinical trials and to commercialization, there is an urgent need to develop simple and safe approaches to image nano-carriers in vivo during the course of treatment, thereby allowing physicians and clinicians to monitor pharmacokinetics, biodistribution and efficacy of the nano-carriers in patients. Liposomes, polymers micelles, nanoparticles, and antibodies have been investigated for imaging applications with the choice of nanocarrier dependent on the drug of interest.

Diamagnetic Chemical Exchange Saturation Transfer (diaCEST) allows detection of a specific pool of exchangeable protons on a molecule. Unlike conventional paramagnetic or superparamagnetic metal-based MRI contrast agents, diaCEST contrast agents are typically small molecules or peptides that do not contain metals, and thereby are potentially less toxic and more biocompatible. Each specific pool of protons can be saturated selectively using radiofrequency pulses, and hence allow for simultaneous monitoring of multiple particle types. Particles loaded with select types of diaCEST agents could therefore be tracked at the same time in vivo.

Previously described diaCEST nanocarriers include hydrophilic diaCEST contrast agents, such as barbituric acid, encapsulated in liposomal particles. However, the use of hydrophilic agents can be problematic for formulating polymeric diaCEST particles. The interior of polymeric particles are typically composed of hydrophobic materials that are designed to encapsulate lipophilic drugs and therefore the loading efficiency of hydrophilic compounds, such as diaCEST contrast agents, can be highly restricted. In addition, the mechanism of diaCEST relies on the free exchange of protons between contrast agents and water molecules. Once the agents are loaded into polymeric particles, their access to water molecules may be severely curtailed due to the limited permeation of water into the particles, thereby diminishing the CEST contrast offered by the agents.

There is a need for nanocarriers which can efficiently incorporate diaCEST agents and allow proton exchange between the diaCEST agent and water molecules.

Therefore, it is an object of the invention to provide nano- and microcarriers which can efficiently incorporate diaCEST agents and allow proton exchange between the diaCEST agent and water molecules and methods of making and using thereof.

It is an object of the invention to provide micro- and/or nanoparticles, such as polymeric micro- and/or nanoparticles, which can efficiently incorporate diaCEST agents, particularly hydrophilic CEST agents, and allow proton exchange between the diaCEST agent and water molecules and methods of making and using thereof.

It is also an object of the invention to provide liposomes, which can efficiently incorporate diaCEST agents and allow proton exchange between the diaCEST agent and water molecules and methods of making and using thereof.

SUMMARY OF THE INVENTION

Surface conjugated diamagnetic Chemical Exchange Saturation Transfer (diaCEST) agent carriers and methods of making and using are described herein. The particles are safe alternatives to conventional paramagnetic or superparamagnetic metal-based MRI contrast agents that are often toxic and therefore not biocompatible. diaCEST can provide simultaneous monitoring of multiple particle types labeled with 'multicolor' diaCEST contrast agents.

In some embodiments the carriers are micro- and/or nanocarriers. In some embodiments, the carriers are micro- and/or nanoparticles. In some embodiments, the particles contain a core. The core can contain or be formed of a biocompatible polymer. In some embodiments, the polymer is biocompatible and biodegradable. In some embodiments, the polymer is biocompatible, biodegradable, and relatively hydrophobic or hydrophobic. The particle further contains a coating of a hydrophilic or amphiphilic material, such as a polymer. In some embodiments, the coating is covalently bound to reactive functional groups of the polymer forming the core (e.g., at the termini). In other embodiments, the core and coating are formed by a block copolymer containing hydrophobic or more hydrophobic blocks that form the core and hydrophilic or more hydrophilic blocks that form the coating. In some embodiments, the one or more diaCEST agents are presented on the surface of the particles. In some embodiments, the one or more diaCEST agents are associated with the coating. In particular embodiments, the one or more diaCEST agents are covalently bound to the coating material. The hydrophilic material on the surface can act as a spacer to enable effective diaCEST imaging of the particles.

In other embodiments, the carriers are liposomes. The liposomes can contain one or more lipids, one or more PEG-conjugated lipids, and/or one or more additional materials that physically and/or chemically stabilize the particles. In some embodiments, the CEST agent is encapsulated within the liposome, associated with the surface of the liposome (e.g., covalently or non-covalently associated with PEG on the surface) or combinations thereof.

In some embodiments, the particles and/or liposomes are mucus penetrating. In other embodiments, the particles and/or liposomes are not mucus penetrating. "Mucus penetrating" as used herein means the particles and/or liposomes are mobile in mucus. "Mobile" as used herein means particles which travel a distance of at least over 10 times its radius (about 100 nm) in a 20 second movie, which corresponds to about 0.1 $\mu m^2/sec$.

The particles/liposomes described herein can exhibit enhanced transport through mucus, such as non-ovulatory human cervicovaginal mucus (CVM). In some embodiments, the particles/liposomes travel through mucus, such as human cervicovaginal mucus, at certain absolute diffusivities. In certain embodiments, the particles/liposomes may travel at diffusivities of at least $1\times10^4$, $2\times10^4$, $5\times10^4$, $1\times10^3$, $2\times10^3$, $5\times10^3$, $1\times10^2$, $2\times10^2$, $4\times10^2$, $5\times10^2$, $6\times10^2$, $8\times10^2$, $1\times10^1$, $2\times10^1$, $5\times10^1$, 2, 1, 0.9, 0.8, 0.7, 0.6, 0.5, 0.4, 0.3, 0.2, or 0.1 $\mu m^2/s$ at a time scale of 1 s. In contrast, non-penetrating particles have a diffusivity of at least about $1\times10^{-4}$ $\mu m^2/s$.

The ability of the particles/liposomes to diffuse through mucus can also be evaluated qualitatively by visual inspection. In some embodiments, the concentration of PEG is about 10 mole percent and at least 50, 60, 70, 80, or 90% of the particles/liposomes are mobile in non-ovulatory CVM at 2 hours and at least 30, 40, 50, 60, or 70% of the particles/liposomes are mobile in non-ovulatory CVM at 15 hours. The particles/liposomes exhibit little or no aggregation. In other embodiments, the concentration of PEG-conjugated lipid is about 20% and at least about 75, 80, 85, 90, 95, 96, 96, 98, or 99% of the particles are mobile in non-ovulatory CVM at 2 hours and at least about 80, 85, 86, 87, 88, 89, 90, 91, 92, 93, 94, 95, 96, 97, 98, or 99% of the particles are mobile in non-ovulatory CVM at 15 hours. The particles/liposomes are well dispersed with little or no aggregation.

In certain embodiments, the particles/liposomes contain a surface-altering agent that inhibits the adsorption of fluorescently labeled avidin, wherein the particle adsorbs less than 99%, 95%, 90%, 70%, 50%, 40%, 30%, 20%, 15%, 10%, 8%, 6%, 5%, 4%, 3%, 2%, 1%, 0.5%, 0.1%, 0.05%, or 0.01% of the amount of fluorescently labeled avidin that is adsorbed by a corresponding particle/liposome lacking the surface-altering agent, as calculated by average maximum fluorescent intensity.

In certain embodiments, the particles/liposomes contain a surface-altering agent that affects the zeta-potential of the particle, wherein the zeta potential of said particle is between −100 mv and 10 mv, between −50 mv and 10 mv, between −25 mv and 10 mv, between −20 mv and 5 mv, between −10 my and 10 mv, between −10 mv and 5 mv, between −5 mv and 5 mv, or even between −2 mv and 2 mv.

The particles and/or liposomes can further contain one or more additional agents, such as one or more therapeutic, prophylactic, and/or diagnostic agents. The one or more additional agents can be covalently or non-covalently associated with the particle and/or liposome, such as the core, the surface, the coating, or combinations thereof. For example, the one or more additional agents can be encapsulated within the core of the particle. In some embodiments, the core is form a hydrophobic material, such as a polymer, having encapsulated therein one or more hydrophobic agents. The one or more additional agents can be associated with the surface, for example, by being covalently bound to the hydrophilic material that forms the coating.

BRIEF DESCRIPTION OF THE DRAWINGS

FIG. 3a is a graph showing normalized saturation profiles for different types of diaCEST contrast agents. (Green: polylysine, PLT; Red: polyargenine, PLR; Blue: polythreonine, PLT). FIGS. 3b-d are CEST MRI results for all 3 types of agents and PBS (blank). CEST MRI results depended on frequency of saturation. Saturation at b) ±3.7 ppm excites all three compounds, at c) ±1.8 ppm mainly PLR, and at d) ±0.8 ppm both PLR and PLT. e) Combinations of images b-d allowed artificial color assignment for all three polypeptides.

DETAILED DESCRIPTION OF THE INVENTION

I. Definitions

Figure 1A:
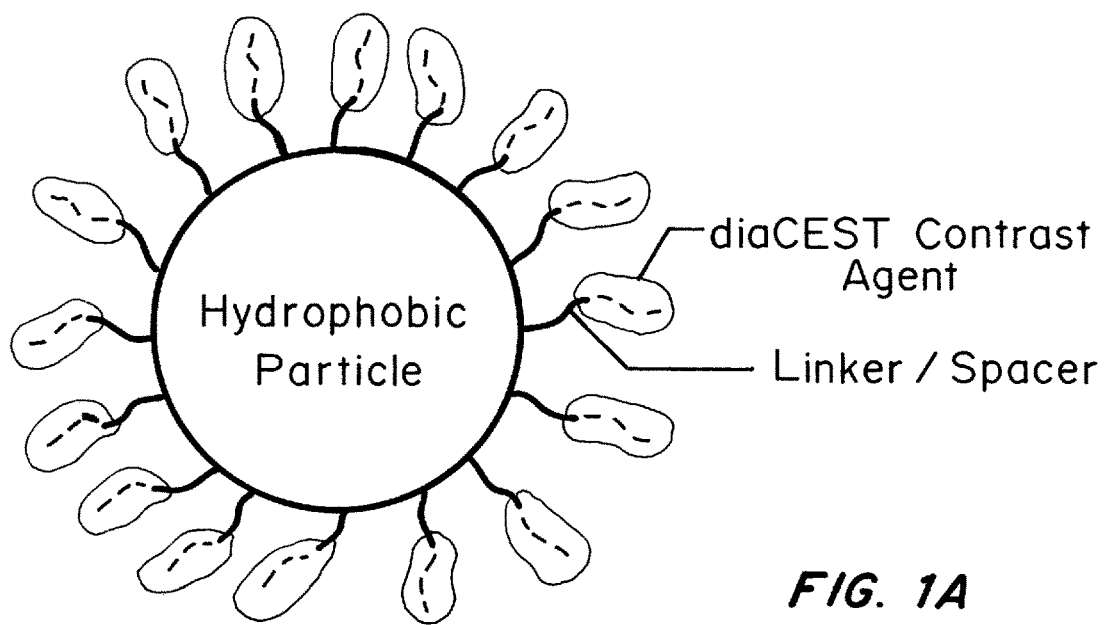
FIG. 1a is a schematic of surface conjugated diaCEST nanoparticles. diaCEST contrast agents (red), which are usually water-soluble and difficult to encapsulate in hydrophobic materials, are conjugated onto the surface of hydrophobic particles (pink) through select linkers (blue).
Figure 1B:
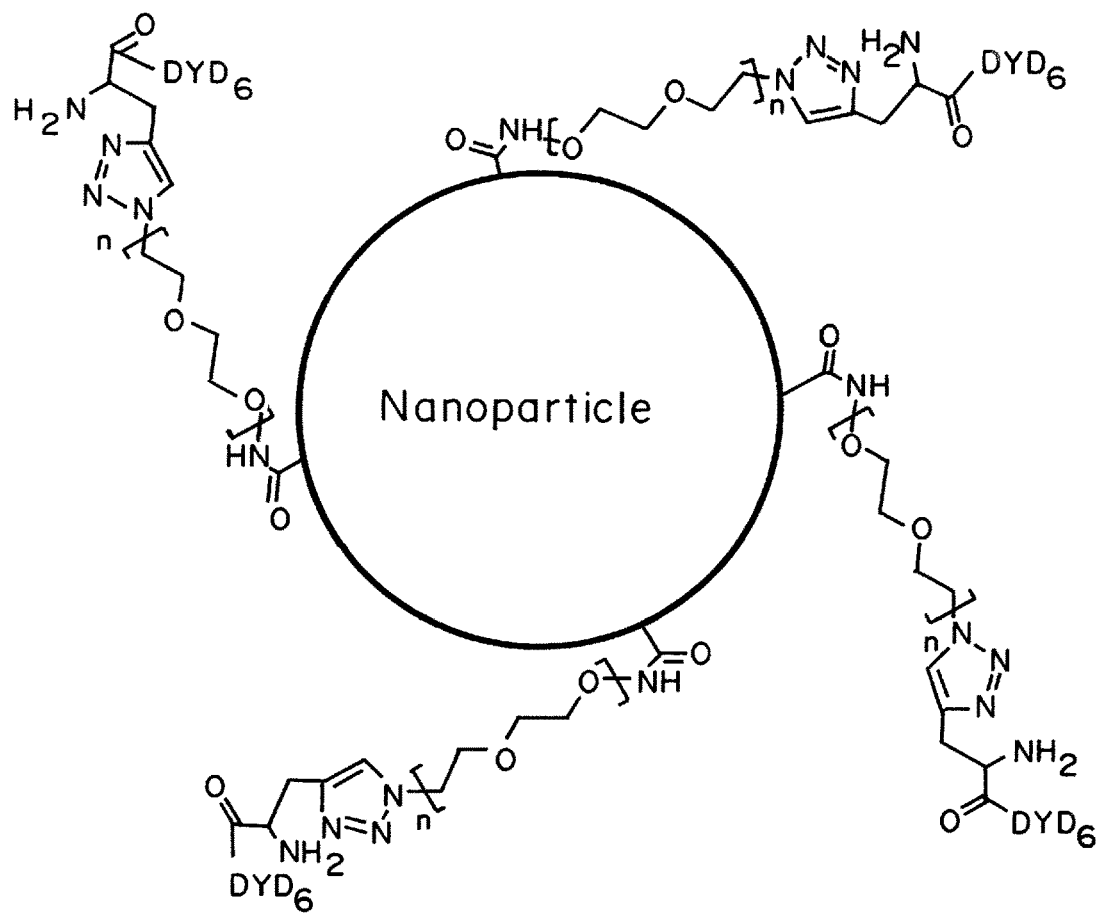
FIG. 1b is a schematic of diaCEST polystyrene (PS) nanoparticles. Poly(Ethylene Glycol) (PEG) molecules with a molecular weight (MW) of ~0.6 kDa or 5.6 kDa were selected as linkers and coupled to the carboxyl groups on the particle surface. (DYD)6 peptides, model diaCEST agent, are conjugated to the PEGs via click chemistry.
Figure 2A:
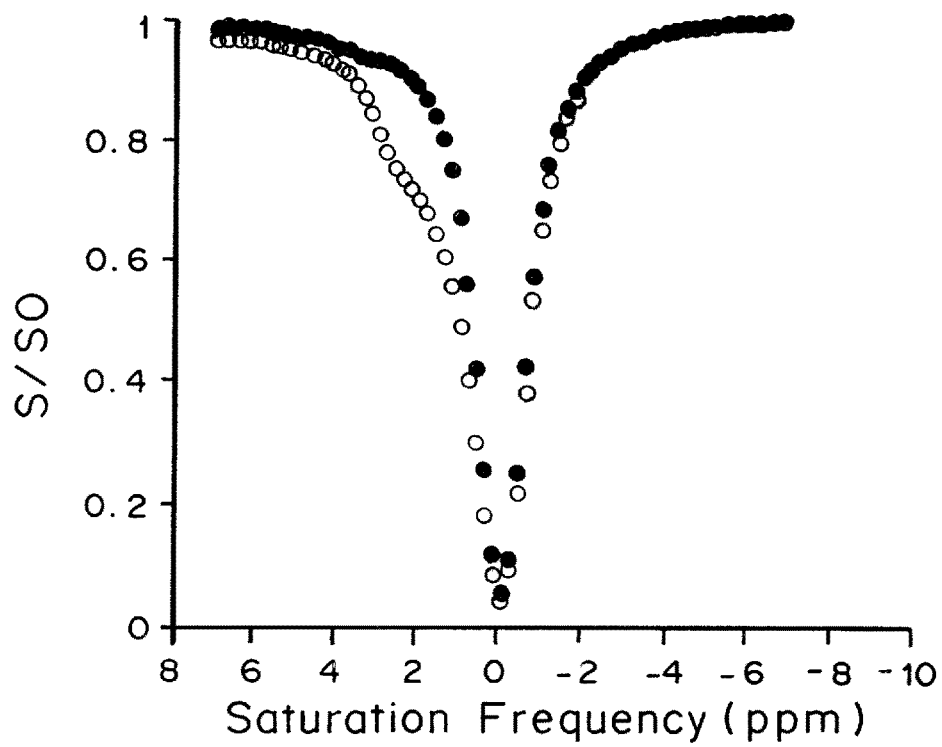
FIG. 2a is a graph showing the Z-spectrum for PS-PEG5.6 k-(DYD)6 and PS-PEG0.6 k-(DYD)6.
Figure 2B:
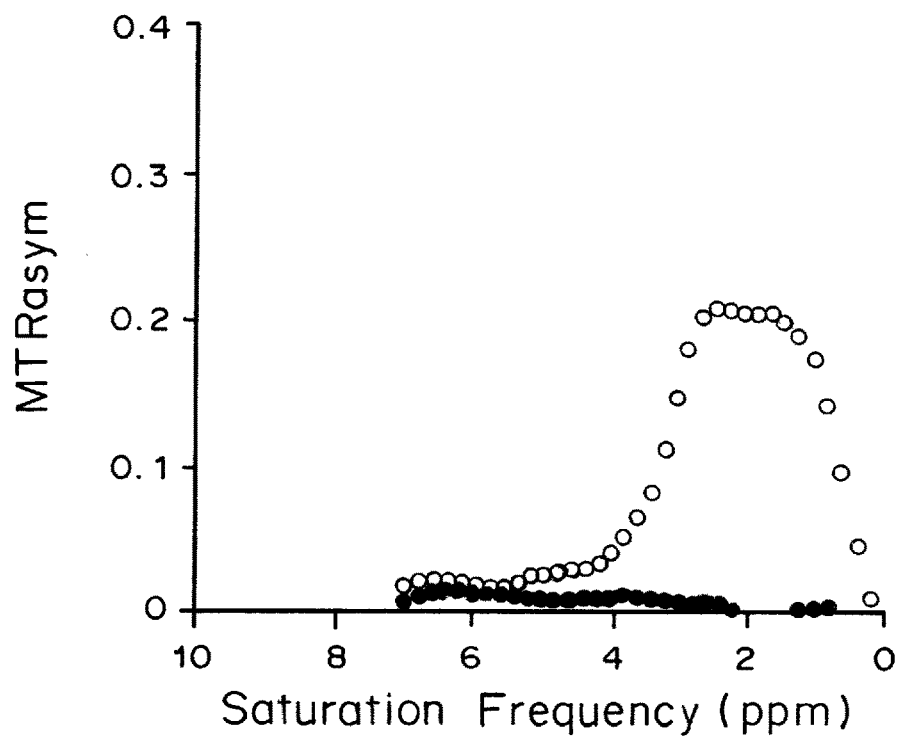
FIG. 2b is a graph showing the Quantified CEST contrast (MTRasym) as a function of saturation frequency for PS-PEG5.6 k-(DYD)6 and PS-PEG0.6 k-(DYD)6.

"Liposome", as used herein, refers to vesicles or particles which possess a lipid bilayer enclosing an aqueous compartment.

"Microparticle", as used herein, generally refers to a particle having a diameter, such as an average diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape are generally referred to as "microspheres".

"Nanoparticle," as used herein, generally refers to a particle of any shape having an average diameter from about 1 nm up to, but not including, about 1 micron, preferably from about 5 nm to about 500 nm, most preferably from about 5 nm to about 300 nm. In some embodiments, the particles have an average diameter from about 100 nm to about 300 nm, preferably from about 100 nm to about 250 nm, more preferably from about 100 nm to about 200 nm. Nanoparticles having a spherical shape are generally referred to as "nanospheres".

"Mean Particle Size," as used herein, generally refers to the statistical mean particle size (diameter) of the particles in a population of particles. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "Homogeneous Size Distribution," are used interchangeably herein and describe a plurality of liposomal nanoparticles or microparticles where the particles have the same or nearly the same diameter or aerodynamic diameter. As used herein, a monodisperse distribution refers to particle distributions in which 75, 76, 77, 78, 79, 80, 81, 82, 83, 84, 85, 86, 86, 88, 89, 90, 91, 92, 93, 94, 95% or greater of the distribution lies within 85, 80, 75, 70, 65, 60, 55, 50, 45, 40, 35, 30, 25, 20, 15, or 10% of the mass median diameter or aerodynamic diameter.

"Hydrophilic," as used herein, refers to the property of having affinity for water. For example, hydrophilic agents and/or polymers (or hydrophilic polymer segments) are agents or polymers (or polymer segments) which are primarily soluble in aqueous solutions and/or have a tendency to absorb water. In general, the more hydrophilic an agent or polymer is, the more that agent or polymer tends to dissolve in, mix with, or be wetted by water. Hydrophilicity can be evaluated by measuring the partition coefficient of a material in an immiscible mixture of water and a hydrophobic solvent, such as 1-octanol. Hydrophilic materials will preferentially partition into the water layer.

"Hydrophobic," as used herein, refers to the property of lacking affinity for, or even repelling water. For example, the more hydrophobic an agent or polymer (or polymer segment), the more that agent or polymer (or polymer segment) tends to not dissolve in, not mix with, or not be wetted by water. Hydrophobicity can be evaluated by measuring the partition coefficient of a material in an immiscible mixture of water and a hydrophobic solvent, such as 1-octanol. Hydrophobic materials will preferentially partition into the 1-octanol layer.

Hydrophilicity and hydrophobicity can be spoken of in relative terms, such as but not limited to a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

"Lipophilic" refers to compounds having an affinity for lipids.

"Amphiphilic" refers to a molecule having hydrophilic and lipophilic (hydrophobic) properties "Pharmaceutically Acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Biocompatible" as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Molecular Weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Active Agent", as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

"Effective Amount" or "Therapeutically Effective Amount", as used herein, refers to an amount of polymer-drug conjugate effective to alleviate, delay onset of, or prevent one or more symptoms of a disease or disorder being treated by the active agent, and/or an amount of polymer-drug conjugate effective to produce a desired diagnostic signal.

"Biocompatible" and "Biologically Compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer" as used herein, generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment.

The term "treating" or preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "targeting moiety" as used herein refers to a moiety that localizes to or away from a specific locale. The moiety may be, for example, a protein, nucleic acid, nucleic acid analog, carbohydrate, or small molecule. The entity may be, for example, a therapeutic compound such as a small molecule, or a diagnostic entity such as a detectable label. The locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including, for example: attached to a monomer of such polymer (by covalent, ionic, or other binding interaction), physical admixture, enveloping the agent in a coating layer of polymer, incorporated into the polymer, distributed throughout the polymeric matrix, appended to the surface of the polymeric matrix (by covalent or other binding interactions), encapsulated inside the polymeric matrix, etc. The term "co-incorporation" or "co-encapsulation" refers to—the incorporation of a therapeutic agent or other material and at least one other therapeutic agent or other material in a subject composition.

Mucus," as used herein, refers to a viscoelastic natural substance containing primarily mucin glycoproteins and other materials, which protects epithelial surface of various organs/tissues, including respiratory, nasal, cervicovaginal, gastrointestinal, rectal, visual and auditory systems. "Sputum," as used herein, refers to highly viscoelastic mucus secretions consist of a variety of macromolecules such as DNA, actins and other cell debris released from dead cells in addition to mucin glycoproteins. "Sputum" is generally present in the pathogenic airways of patients afflicted by obstructive lung diseases, including but not limited to, asthma, COPD and CF. "CF mucus" and "CF sputum," as used herein, refer to mucus and sputum, respectively, from a patient suffering from cystic fibrosis. In some embodiments, the mucus is non-ovulatory human cervicovaginal mucus (CVM).

"Mucus Degrading Agent," as used herein, refers to a substance which increases the rate of mucus clearance when administered to a patient. Mucus degrading agents are known in the art. See, for example, Hanes, J. et al. Gene Delivery to the Lung. in Pharmaceutical Inhalation Aerosol Technology, Marcel Dekker, Inc., New York: 489-539 (2003). Examples of mucus degrading agents include N-acetylcysteine (NAC), which cleaves disulfide and sulfhydryl bonds present in mucin. Other mucus degrading agents include mugwort, bromelain, papain, clerodendrum, acetylcysteine, bromhexine, carbocisteine, eprazinone, mesna, ambroxol, sobrerol, domiodol, denufosol, letosteine, stepronin, tiopronin, gelsolin, thymosin P4, neltenexine, erdosteine, and various DNases including rhDNase.

II. Nano- and Microcarriers

A. Particles

In one embodiment, the carriers are particles, such as micro- and/or nanoparticles. The size ranges for these particles are defined above. In some embodiments, the particles are nanoparticles having a diameter less than 500 nm.

1. Core

The particles describes herein contain a core formed of or containing one or more biocompatible polymers. In some embodiments, the polymer is hydrophobic. In other embodiments, the polymer is also biodegradable.

Examples of biocompatible polymers include but are not limited to polystyrenes; poly(hydroxy acid); poly(lactic acid); poly(glycolic acid); poly(lactic acid-co-glycolic acid); poly(lactic-co-glycolic acid); poly(lactide); poly(glycolide); poly(lactide-co-glycolide); polyanhydrides; polyorthoesters; polyamides; polycarbonates; polyalkylenes; polyethylenes; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; polyvinyl chloride); polyvinylpyrrolidone; polysiloxanes; polyvinyl alcohols); poly(vinyl acetate); polyurethanes; copolymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxyethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly (ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly(lactide-co-caprolactone); blends of poly(lactide-co-caprolactone); hydroxyethyl methacrylate (HEMA); copolymers of HEMA with acrylate; copolymers of HEMA with polymethylmethacrylate (PMMA); polyvinylpyrrolidone/vinyl acetate copolymer (PVP/VA); acrylate polymers/copolymers; acrylate/carboxyl polymers; acrylate hydroxyl and/or carboxyl copolymers; polycarbonate-urethane polymers; silicone-urethane polymers; epoxy polymers; cellulose nitrates; polytetramethylene ether glycol urethane; polymethylmethacrylate-2-hydroxyethylmethacrylate copolymer; polyethylmethacrylate-2-hydroxyethylmethacrylate copolymer; polypropylmethacrylate-2-hydroxyethylmethacrylate copolymer; polybutylmethacrylate-2-hydroxyethylmethacrylate copolymer; polymethylacrylate-2-hydroxyethylmethacrylate copolymer; polyethylacrylate-2-hydroxyethylmethacrylate copolymer; polypropylacrylate-2-hydroxymethacrylate copolymer; polybutylacrylate-2-hydroxyethylmethacrylate copolymer; copolymermethylvinylether maleic anhydride copolymer; poly (2-hydroxyethyl methacrylate) acrylate polymer/copolymer; acrylate carboxyl and/or hydroxyl copolymer; olefin acrylic acid copolymer; ethylene acrylic acid copolymer; polyamide polymers/copolymers; polyimide polymers/copolymers; ethylene vinylacetate copolymer; polycarbonate urethane; silicone urethane; polyvinylpyridine copolymers; polyether sulfones; polygalactia poly-(isobutyl cyanoacrylate), and poly(2-hydroxyethyl-L-glutamine); polydimethyl siloxane; poly(caprolactones); poly(ortho esters); polyamines; polyethers; polyesters; polycarbamates; polyureas; polyimides; polysulfones; polyacetylenes; polyetheneimines; polyisocyanates; polyacrylates; polymethacrylates; polyacrylonitriles; polyarylates; and combinations, copolymers and/or mixtures of two or more of any of the foregoing.

The biodegradable polymer can contain a synthetic polymer, although natural polymers also can be used. The polymer can be, for example, poly(lactic-co-glycolic acid) (PLGA), polystyrene or combinations thereof. The polystyrene can, for example, be modified with carboxyl groups. Other examples of biodegradable polymers include poly (hydroxy acid); poly(lactic acid); poly(glycolic acid); poly (lactic acid-co-glycolic acid); poly(lactide); poly(glycolide);

poly(lactide-co-glycolide); polyanhydrides; polyorthoesters; polyamides; polycarbonates; polyalkylenes; polyethylene; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; polyvinyl chloride); polyvinylpyrrolidone; polysiloxanes; poly(vinyl alcohols); polyvinyl acetate); polyurethanes; copolymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly(ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly(lactide-co-caprolactone); blends of poly(lactide-co-caprolactone); polygalactin; poly-(isobutyl cyanoacrylate); poly(2-hydroxyethyl-L-glutam-nine); and combinations, copolymers and/or mixtures of one or more of any of the foregoing.

As used herein, "derivatives" include polymers having substitutions, additions of chemical groups and other modifications routinely made by those skilled in the art. For example, functional groups on the polymer can be capped to alter the properties of the polymer and/or modify (e.g., decrease or increase) the reactivity of the functional group. For example, the carboxyl termini of carboxylic acid contain polymers, such as lactide- and glycolide-containing polymers, may optionally be capped, e.g., by esterification, and the hydroxyl termini may optionally be capped, e.g. by etherification or esterification.

2. Surface Altering Agent

The particles described herein contain a surface altering agent which coats or encapsulate the particle core. In some embodiments, the surface altering agent is hydrophilic or contains hydrophilic moieties or blocks. In some embodiments, the particles contain a coating on the surface, wherein the coating molecules have hydrophilic regions and, optionally, hydrophobic regions. The coating can be disposed on the surface of the particle, for example by bonding, adsorption or by complexation. The coating can also be intermingled or dispersed within the particle as well as disposed on the surface of the particle. In those embodiments, wherein the coating contains one or more hydrophobic moieties, these moieties may form the core of the particles. The hydrophilic moiety acts as a spacer to provide effective diaCEST imaging of the particles.

The coating can be, for example, polyethylene glycol, polyvinyl alcohol (PVA), or similar substances. The coating can be, for example, vitamin E-PEG 1 k or vitamin E-PEG 5 k or the like. Vitamin E-PEG 5 k can help present a dense coating of PEG on the surface of a particle. The coating can also include nonionic surfactants such as those composed of polyaklyene oxides, e.g., polyoxyethylene (PEO), also referred to herein as polyethylene glycol; or polyoxypropylene (PPO), also referred to herein as polypropylene glycol (PPG), and can include co-polymers of more than one alkylene oxide. The copolymers can be, for example, random copolymers, block copolymers or graft copolymers.

In some embodiments, the coating includes a polyoxyethylene-polyoxypropylene copolymer, e.g., block copolymers of ethylene oxide and propylene oxide, (i.e., poloxamers). Examples of poloxamers suitable for use in the coatings include, for example, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E10i to about E)06 P7o E106, or about E101 P56 E10i, or about E106 P70 E106, with an average molecular mass of about 10,000 to about 15,000 Da, or about 12,000 to about 14,000 Da, or about 12,000 to about 13,000 Da, or about 12,600 Da. For example, the NF forms of poloxamers or Pluronic® polymers can be used.

In some embodiments, the coating can be, for example Pluronic® PI 03 or Pluronic®P105. Pluronic® P103 is a block copolymer with an average molecular mass of about 3,000 Da to about 6,000 Da, or about 4,000 Da to about 6,000 Da, or about 4,950 Da. Pluronic® PI 05 is a block copolymer with an average molecular mass of about 5,000 Da to about 8,000 Da, or about 6,000 Da to about 7,000 Da, or about 6,500 Da.

In some embodiments, the coating is non-covalently associated with the particle. This association can be held together by any force or mechanism of molecular interaction that permits two substances to remain in substantially the same positions relative to each other, including intermolecular forces, dipole-dipole interactions, van der Waals forces, hydrophobic interactions, electrostatic interactions and the like. In some embodiments, the coating is adsorbed onto the particle. According to representative embodiments, a non-covalently bound coating can be comprised of portions or segments that promote association with the particle, for example by electrostatic or van der Waals forces. In some embodiments, the interaction is between a hydrophobic portion of the coating and the particle. Embodiments include particle coating combinations which, however attached to the particle, present a hydrophilic region, e.g. a PEG rich region, to the environment around the particle coating combination. The particle coating combination can provide both a hydrophilic surface and an uncharged or substantially neutrally-charged surface, which can be biologically inert.

Suitable coatings for use according to the compositions and methods disclosed herein can be made up of molecules having hydrophobic regions as well as hydrophilic regions. Without wishing to be bound by any particular theory, it is believed that the hydrophobic regions of the coating molecules are able to form adsorptive interactions with the surface of the particle, and thus maintain a non-covalent association with it, while the hydrophilic regions orient toward the surrounding, frequently aqueous, environment. In some embodiments the hydrophilic regions are characterized in that they avoid or minimize adhesive interactions with substances in the surrounding environment. Suitable hydrophobic regions in the coatings can include, for example, PPO, vitamin E and the like, either alone or in combination with each other or with other substances. Suitable hydrophilic regions in the coatings can include, for example, PEG, heparin, polymers that form hydrogels and the like, alone or in combination with each other or with other substances.

Representative coatings according to the compositions and methods disclosed herein can include molecules having, for example, hydrophobic segments such as PPO segments with molecular weights of at least about 1.8 kDa, or at least about 2 kDa, or at least about 2.5 kDa, or at least about 3 kDa, or at least about 3.5 kDa, or at least about 4.0 kDa, or at least about 4.5 kDa, or at least about 5.0 kDa or more. In some embodiments, the coatings can have PPO segments with molecular weights of from about from about 1.8 kDa to about 10 kDa, or from about 2 kDa to about 5 kDa, or from about 2.5 kDa to about 4.5 kDa, or from about 2.5 kDa to about 3.5 kDa. In some embodiments, at least about 10%, or at least about 25%, or at least about 50%, or at least about 75%, or at least about 90%, or at least about 95%, or at least about 99% or more of the hydrophobic regions in these coatings have molecular weights within these ranges.

In some embodiments, the coatings are biologically inert. Compounds that generate both a hydrophilic surface and an uncharged or substantially neutrally-charged surface can be biologically inert.

In some embodiments, the coating can include, for example, one or more of the following: anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin), mucolytic agents, N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin P4, dornase alfa, neltenexine, erdosteine, various DNases including rhDNase, agar, agarose, alginic acid, amylopectin, amylose, beta-glucan, callose, carrageenan, cellodextrins, cellulin, cellulose, chitin, chitosan, chrysolaminarin, curdlan, cyclodextrin, dextrin, ficoll, fructan, fucoidan, galactomannan, gellan gum, glucan, glucomannan, glycocalyx, glycogen, hemicellulose, hydroxyethyl starch, kefiran, laminarin, mucilage, glycosaminoglycan, natural gum, paramylon, pectin, polysaccharide peptide, schizophyllan, sialyl lewis x, starch, starch gelatinization, sugammadex, xanthan gum, xyloglucan, L-phosphatidylcholine (PC), 1,2-dipalmitoyl-phosphatidycholine (DPPC), oleic acid, sorbitan trioleate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, polyoxyethylene (4) lauryl ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, sunflower seed oil, lecithin, oleic acid, sorbitan trioleate, and combinations of two or more of any of the foregoing.

The particle-coating combinations can be made up of any combination of particle and coating substances disclosed or suggested herein.

In some embodiments, the coating is associated with the particle, either through covalent or non-covalent interactions with the particle. Coatings that can be covalently bound to the particle include, for example, PEG. PEG can be covalently bound to any suitable polymer that can be included in the particle. An example of a polymer that can be coated with PEG is polystyrene. Other particles that can be PEGylated are known in the art.

In some embodiments, the coating is or contains a polyalkylene oxide, such as polyethylene glycol (PEG). In some embodiments, PEG is covalently or non-covalently associated with the surface. In some embodiments, PEG is present as blocks in a block copolymer containing hydrophobic blocks that form the core of the particle and present PEG on the surface. In other embodiments, PEG is covalently bound (e.g., grafted) to functional groups on the polymer that forms the core. The molecular weight of PEG can vary. However, in some embodiments, the molecular weight of PEG is from about 500 Daltons to about 10,000 Daltons, preferably from about 1000 Daltons to about 10,000 Daltons, preferably from about 2000 Daltons to about 10,000 Daltons, more preferably from about 3,000 Daltons to about 10,000 Daltons, most preferably from about 5,000 Daltons to about 10,000 Daltons. In some embodiments, the molecular weight is greater than about 5,000 Daltons.

The density of the surface altering agent, such as PEG, can vary. In some embodiments, the density of the surface altering polymer chain, block, or moiety is from about 0.1 to about 1000 chains/blocks/moieties per 100 $nm^2$. In some embodiments, the density is at least about 10 chains/blocks/moieties/100 $nm^2$.

The surface altering agent can alter or modify the surface charges of the particles. The surface charge can be negative, neutral, or positive depending on the nature of the surface altering agent, which can be selected based upon the desired application. In some embodiments, the surface charge, typically expressed as the zeta potential, is from about −100 mV to about 100 mV, preferably −75 mV to about 75 mV, more preferably −50 mV to about 50 mV, more preferably −25 mV to about 25 mV, most preferably from about −10 mV to about 10 mV.

B. Liposomes

In some embodiments, the nano- or microcarrier is a liposome. A liposome is a synthetic vesicle or particle containing a lipid bilayer. Liposomes can be used for drug delivery. The major types of liposomes are the multilamellar vesicle (MLV), the small unilamellar vesicle (SUV), the large unilamellar vesicle (LUV), and the cochleate vesicle. In some embodiments, the liposomes contain one or more lipids, one or more PEG-conjugated lipids, and/or one or more additional materials that physically and/or chemically stabilize the particles.

1. Lipids

The liposomes described herein contain one or more lipid components. Lipids are naturally occurring, synthetic, or semi-synthetic molecules that include fats, waxes, sterols, fat-soluble vitamins (such as vitamins A, D, E, and K), monoglycerides, diglycerides, triglycerides, phospholipids, and others.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from two distinct types of biochemical subunits or "building-blocks": ketoacyl and isoprene groups.

Using this approach, lipids may be divided into eight categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

The concentration of the lipid is from about 20 to 100 mole percent, preferably about 20 to about 95 mole percent, more preferably from about 20 to about 90 mole percent, most preferably from about 20 to about 80 mole percent. In some embodiments, the concentration may be from about 40 to about 70 mole percent, preferably from about 40 to about 60 mole percent.

i. Fatty Acids

Fatty acids, or fatty acid residues when they form part of a lipid, are a diverse group of molecules which can be prepared synthetically or synthesized naturally by chain-elongation of an acetyl-CoA primer with malonyl-CoA or methylmalonyl-CoA groups in a process called fatty acid synthesis. Fatty acids are made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. Where a double bond exists, there is the possibility of either a cis or trans geometric isomerism, which significantly affects the molecule's configuration. Cis-double bonds cause the fatty acid chain to bend, an effect that is compounded with more double bonds in the chain. Most naturally occurring fatty acids are of the cis configuration, although the trans form does exist in some natural and partially hydrogenated fats and oils. Other major lipid classes in the fatty acid category are the fatty esters and fatty amides.

ii. Glycerolipids

Glycerolipids are composed mainly of mono-, di-, and tri-substituted glycerols, the most well-known being the fatty acid triesters of glycerol, called triglycerides. The word "triacylglycerol" is sometimes used synonymously with "triglyceride", though the latter lipids contain no hydroxyl group. In these compounds, the three hydroxyl groups of glycerol are each esterified, typically by different fatty acids.

Additional subclasses of glycerolipids are represented by glycosylglycerols, which are characterized by the presence of one or more sugar residues attached to glycerol via a glycosidic linkage. Examples of structures in this category are the digalactosyldiacylglycerols found in plant membranes and seminolipid from mammalian sperm cells.

iii. Glycerophospholipids

Glycerophospholipids, usually referred to as phospholipids, are ubiquitous in nature and are key components of the lipid bilayer of cells, as well as being involved in metabolism and cell signaling. Most phospholipids contain a diglyceride, a phosphate group, and a simple organic molecule such as choline; one exception to this rule is sphingomyelin, which is derived from sphingosine instead of glycerol.

The structure of the phospholipid molecule generally consists of hydrophobic tails and a hydrophilic head. The 'head' is attracted to water, while the hydrophobic 'tails' are repelled by water and are forced to aggregate. The hydrophilic head contains the negatively charged phosphate group, and may contain other polar groups. The hydrophobic tail usually consists of long fatty acid hydrocarbon chains. When placed in water, phospholipids form a variety of structures depending on the specific properties of the phospholipid. Lipid bilayers occur when hydrophobic tails line up against one another, forming a membrane of hydrophilic heads on both sides facing the water.

Glycerophospholipids may be subdivided into distinct classes, based on the nature of the polar headgroup at the sn-3 position of the glycerol backbone in eukaryotes and eubacteria, or the sn-1 position in the case of archaebacteria. Examples of glycerophospholipids found in biological membranes are phosphatidylcholine (also known as PC, GPCho or lecithin), phosphatidylethanolamine (PE or GPEtn) and phosphatidylserine (PS or GPSer).

In eukaryotes, phospholipids are generally classified into two types: diacylglycerides and phosphingolipids. Examples of diacylglycerides include, but are not limited to, phosphatidic acid (phosphatidate) (PA), phosphatidylethanolamine (cephalin) (PE), phosphatidylcholine (lecithin) (PC), phosphatidylserine (PS), and phosphoinositides, such as phosphatidylinositol (PI), phosphatidylinositol phosphate (PIP), phosphatidylinositol bisphosphate (PIP2) and, phosphatidylinositol triphosphate (PIP3). Examples of phospingolipids include, but are not limited to, ceramide phosphorylcholine (Sphingomyelin) (SPH), ceramide phosphorylethanolamine (Sphingomyelin) (Cer-PE), and Ceramide phosphoryllipid.

Other phospholipids that can be used are shown in Table 1 below.

TABLE 1

| Phospholipids | | | |
|---|---|---|---|
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . .) (Sodium Salt) | Phosphatidylglycerol |
| DLOPC | 998-06-1 | 1,2-Dilinoleoyl-sn-glycero-3-phosphocholine | Phosphatidylcholine |
| DLPA-NA | | 1,2-Dilauroyl-sn-glycero-3-phosphate (Sodium Salt) | Phosphatidic acid |
| DLPC | 18194-25-7 | 1,2-Dilauroyl-sn-glycero-3-phosphocholine | Phosphatidylcholine |

TABLE 1-continued

| Phospholipids | | | |
|---|---|---|---|
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . .) (Sodium Salt) | Phosphatidylglycerol |
| DLPG-NH4 | | 1,2-Dilauroyl-sn-glycero-3[Phospho-rac-(1-glycerol . . .) (Ammonium Salt) | Phosphatidylglycerol |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . .) (Sodium Salt) | Phosphatidylglycerol |
| DMPG-NH4 | | 1,2-Dimyristoyl-sn-glycero-3[Phospho-rac-(1-glycerol . . .) (Ammonium Salt) | Phosphatidylglycerol |
| DMPG-NH4/NA | | 1,2-Dimyristoyl-sn-glycero-3[Phospho-rac-(1-glycerol . . .) (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |
| DOPG-NA | 62700-69-0 | 1,2-Dioleoyl-sn-glycero-3[Phospho-rac-(1-glycerol . . .) (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol . . .) (Sodium Salt) | Phosphatidylglycerol |
| DPPG-NH4 | 73548-70-6 | 1,2-Dipalmitoyl-sn-glycero-3[Phospho-rac-(1-glycerol . . .) (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . .) (Sodium Salt) | Phosphatidylglycerol |
| DSPG-NH4 | 108347-80-4 | 1,2-Distearoyl-sn-glycero-3[Phospho-rac-(1-glycerol . . .) (Ammonium Salt) | Phosphatidylglycerol |
| DSPS-NA | | 1,2-Distearoyl-sn-glycero-3-phosphoserine (Sodium Salt) | Phosphatidylserine |
| Egg Sphingomyelin empty Liposome | | | |
| EPC | | Egg-PC | Phosphatidylcholine |
| HEPC | | Hydrogenated Egg PC | Phosphatidylcholine |
| HSPC | | High purity Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |

TABLE 1-continued

| | | Phospholipids | |
|---|---|---|---|
| Milk Sphingomyelin MPPC | | 1-Myristoyl-2-palmitoyl-sn-glycero 3-phosphocholine | Phosphatidylcholine |
| MSPC | | 1-Myristoyl-2-stearoyl-sn-glycero-3-phosphocholine | Phosphatidylcholine |
| PMPC | | 1-Palmitoyl-2-myristoyl-sn-glycero-3-phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol) . . .] (Sodium Salt) | Phosphatidylglycerol |
| PSPC | | 1-Palmitoyl-2-stearoyl-sn-glycero-3-phosphocholine | Phosphatidylcholine |
| SMPC | | 1-Stearoyl-2-myristoyl-sn-glycero-3-phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholine |

In some embodiments, the lipid component is one or more phospholipids. In some embodiments, the lipid is, or contains, phosphatidylcholine (PC, e.g., egg PC or hydrogenated soy PC). The concentration of the phospholipid is from about 20 to 100 mole percent, preferably about 20 to about 95 mole percent, more preferably from about 20 to about 90 mole percent, most preferably from about 20 to about 80 mole percent. In some embodiments, the concentration may be from about 40 to about 70 mole percent, preferably from about 40 to about 60 mole percent.

iv. Sphingolipids

Sphingolipids are a complicated family of compounds that share a common structural feature, a sphingoid base backbone that is synthesized de novo from the amino acid serine and a long-chain fatty acyl CoA, then converted into ceramides, phosphosphingolipids, glycosphingolipids and other compounds. The major sphingoid base of mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms.

The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

v. Sterol Lipids

Sterol lipids, such as cholesterol and its derivatives, are an important component of membrane lipids, along with the glycerophospholipids and sphingomyelins. The steroids are all derived from the same fused four-ring core structure. Other examples of sterols are the bile acids and their conjugates. The plant equivalents are the phytosterols, such as β-sitosterol, stigmasterol, and brassicasterol.

vi. Prenol Lipids

Prenol lipids are synthesized from the five-carbon-unit precursors isopentenyl diphosphate and dimethylallyl diphosphate. The simple isoprenoids (linear alcohols, diphosphates, etc.) are formed by the successive addition of C5 units, and are classified according to number of these terpene units. Structures containing greater than 40 carbons are known as polyterpenes. Carotenoids are important simple isoprenoids that function as antioxidants and as precursors of vitamin A Another biologically important class of molecules is exemplified by the quinones and hydroquinones, which contain an isoprenoid tail attached to a quinonoid core of non-isoprenoid origin. Vitamin E and vitamin K, as well as the ubiquinones, are examples of this class. Prokaryotes synthesize polyprenols (called bactoprenols) in which the terminal isoprenoid unit attached to oxygen remains unsaturated, whereas in animal polyprenols (dolichols) the terminal isoprenoid is reduced.

vii. Saccharolipids

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains.

2. PEG-Conjugated Lipids

The liposomes may also contain a PEG-conjugated lipid. The lipid can be conjugated to PEG itself or a copolymer containing PEG, such as PEO-PPO copolymer available under the tradename PLURONIC. Other materials, such as polymers, surfactants, nucleic acids, proteins, etc., can be used in place of or in combination with PEG provided the material enhances or facilitate diffusion through mucus.

The PEG-conjugated lipid can be a pegylated form of any of the lipids discussed above. In some embodiments, the PEG-conjugated lipid is a PEG-conjugated phospholipid. In particular embodiments, the PEG-conjugated phospholipid is PEG-phosphatidylethanolamine (PEG-PE). The concentration of the PEG-conjugated lipid in the liposome is at least about 1, 3, 5, or 10 mole percent, for example, about 10 to about 30 mole percent, preferably about 10 mole percent to about 20 mole percent.

The molecular weight of PEG can vary. In some embodiments, the molecular weight of PEG is from about 500 Daltons to about 10,000 Daltons, preferably from about 500 Daltons to about 5,000 Daltons, more preferably from about 1,000 Daltons to about 5,000 Daltons, most preferably from about 2,000 Daltons to about 4,000 Daltons. In particular embodiments, the molecular weight of PEG is about 2000 Daltons.

3. Stabilizer

The liposome can also contain one or more stabilizers. Stabilizers are components or additional components in the liposomes that reduce or prevent vesicle destabilization and/or opsonization and concomitant release of encapsulated agents or drugs. For example, stabilizers, such as cholesterol and other materials, enhance the mechanical strength of the lipid bilayer. Other materials include one or more of the lipids described above.

The concentration of the stabilizer(s) is at least about 5 mole percent, preferably at least about 10 mole percent, more preferably at least about 20 mole percent, most preferably at least about 30 mole percent. In some embodiments, the concentration of the stabilizer is from about 5 mole % to about 50 mole %. In particular embodiment, the concentration of the stabilizer is about 25, 50, or 70 mole percent. In a more particular embodiment, the concentration of the stabilizer is about 25 mole percent.

In some embodiments, the stabilizer is cholesterol and is present in a concentration as described above. Other suitable stabilizers include ganglioside $G_{M1}$. In other embodiments, the stabilizer can be the PEG-conjugated lipid and thus an additional stabilizer or stabilizers is not required.

4. Surface Density of Polyethylene Glycol (PEG)

The concentration of PEG-conjugated lipid is discussed above with reference to the mole percent of PEG-conjugated lipid. The amount of PEG can also be described in terms of surface density. Nuclear magnetic resonance (NMR) can be used to assess the surface PEG density on PEG-containing liposomal nanoparticles described herein, both qualitatively and quantitatively (PEG peak typically observed ~3.65 ppm). In some embodiments, PEG surface density can be controlled by preparing the particles from a mixture of pegylated and non-pegylated lipids. For example, the surface density of PEG on liposomal nanoparticles can be precisely controlled by preparing particles from a mixture of PEG-conjugated lipid and non-PEG-conjugated lipid. Quantitative $^1H$ nuclear magnetic resonance (NMR) can be used to measure the surface PEG density on liposomal nanoparticles.

The density of the coating can be varied based on a variety of factors including the surface altering material and the composition of the particle. In one embodiment, the density of the surface altering material, such as PEG, as measured by $^1H$ NMR is at least, 0.1, 0.2, 0.5, 0.8, 1, 2, 5, 8, 10, 15, 20, 25, 40, 50, 60, 75, 80, 90, or 100 chains per $nm^2$. The range above is inclusive of all values from 0.1 to 100 units per $nm^2$. In particular embodiments, the density of the surface altering material, such as PEG, is from about 1 to about 25 chains/$nm^2$, from about 1 to about 20 chains/$nm^2$, from about 5 to about 20 chains/$nm^2$, from about 5 to about 18 chains/$nm^2$, from about 5 to about 15 chains/$nm^2$, or from about 10 to about 15 chains/$nm^2$. The concentration of the surface altering material, such as PEG, can also be varied. In particular embodiments, the density of the surface-altering material (e.g., PEG) is such that the surface-altering material (e.g. PEG) adopted an extended brush configuration. In other embodiments, the mass of the surface-altering moiety is at least 1/10,000, 1/7500, 1/5000, 1/4000, 1/3400, 1/2500, 1/2000, 1/1500, 1/1000, 1/750, 1/500, 1/250, 1/200, 1/150, 1/100, 1/75, 1/50, 1/25, 1/20, 1/5, 1/2, or 9/10 of the mass of the particle. The range above is inclusive of all vales from 1/10,000 to 9/10.

It has been found that significantly higher concentrations of PEG-conjugated lipids are necessary to impart mucus-penetrating properties. The concentration of PEG-conjugated lipids is typically at least about 8 or about 10 mole percent, for example from about 8 or about 10 to about 30 mole percent, preferably from about 8 or about 10 mole percent to about 20 mole percent.

C. DiaCEST Agents

The particles described herein contain one or more diaCEST agents associated with the particles. In some embodiments, the diaCEST agent(s) is a hydrophilic agent. In some embodiments, the diaCEST agent(s) is a hydrophilic agent and is covalently associated with the particle. In some embodiments, the diaCEST agent(s) is a hydrophilic agent and the agent is covalently associated with the coating on the particle. For example, the agent or agents can be covalently bound to PEG.

Exemplary agents include, but are not limited to, L-arginine, barbituric acid, analogs of barbituric acid (e.g., ring substitution with F, COOH, carbonyl, attachment of phospholipid, or attachment of one or more barbituric acid or derivative thereof to a peptide), salicylic acid analogs such as 4-amino-salicyllic acid; anthranillic acid analogs such as 2-(methyl-sulfonamido) benzoic acid; heterocyclic compounds such imidazole and derivatives thereof (ring substitution with Br, COOH, carbonyl, phospholipid, or attachment of one or more imidazole or derivative thereof to a peptide), such as 4,5-bis[(Lys)carbonyl]-1H-imidazole, peptides rich in backbone NH, guanidyl $NH_2$, and/or OH protons, such as lysine-glycine or derivatives thereof (attach to phospholipid or include multiple copies in peptide); amino acids, such as 1-arginine (attach to phospholipid or include multiple copies in peptide), sugars or carbohydrates having CEST-detectable OH groups (e.g., glycogen, glucose, myoinositol), glutamate, creatine, propargylglycine-W-$(DYD)_6$-$NH_2$, and many polycationic peptides (e.g., poly-L-lysine). In some embodiments, the agent is L-arginine, poly-L-lysine, or barbituric acid. In particular embodiments, the agent is barbituric acid.

Exemplary peptide CEST agents that are rich in backbone $NH_2$, guanidyl $NH_2$, and/or OH protons include, but are not limited to, KS, KSS, KSSS, TK, TTTTTK, TTTK, TTK, K, KGGG, KGG, KH, KG, DSSSSS, R, PS, RT, RG, RTT, RTTT, RS, RH, ETT, DTTTTT, ETTTTT, ETTT, DTTT, DSSS, DTT, T, ET, DS, DT, and combinations thereof, wherein K=lysine, R=arginine, S=serine, G=glycine, H=histidine, D=aspartic acid, and E=glutamine.

Exemplary derivatives of barbituric acid include, but are not limited to, the compounds shown below:

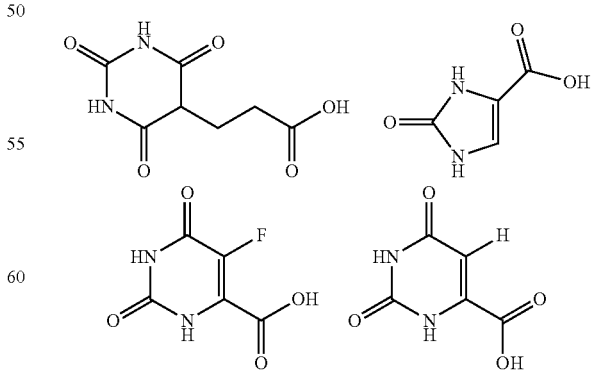

The agents described above can be conjugated to amino acids side chains, such as lysine, as shown below:

Scheme 1
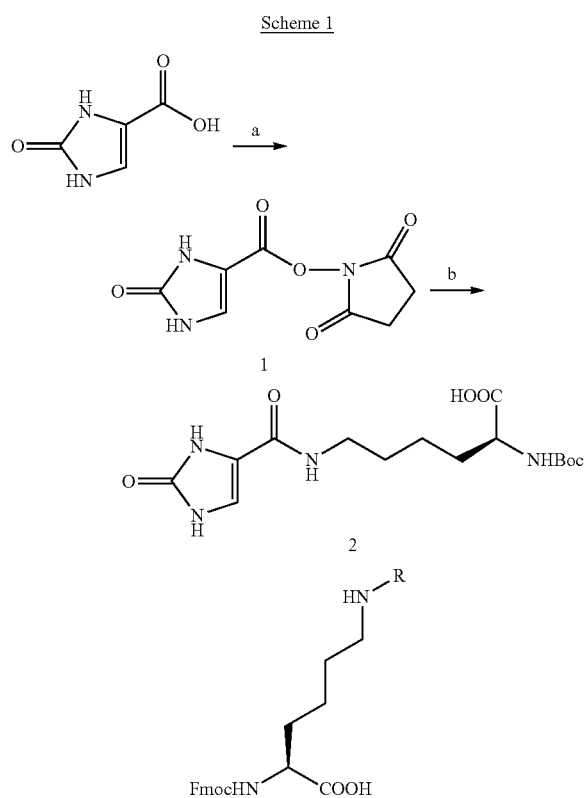
Reagents and conditions: (a) N-hydroxysuccinimide, DCC, DMF, (b) Lys(Boc)—COOH, TEA, DMF
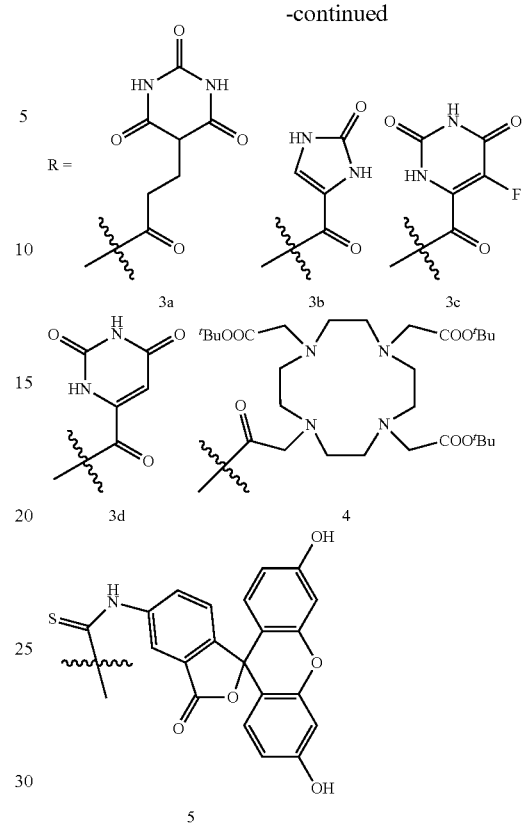
Conjugation of CEST agents to lipids is shown below:
Scheme 2
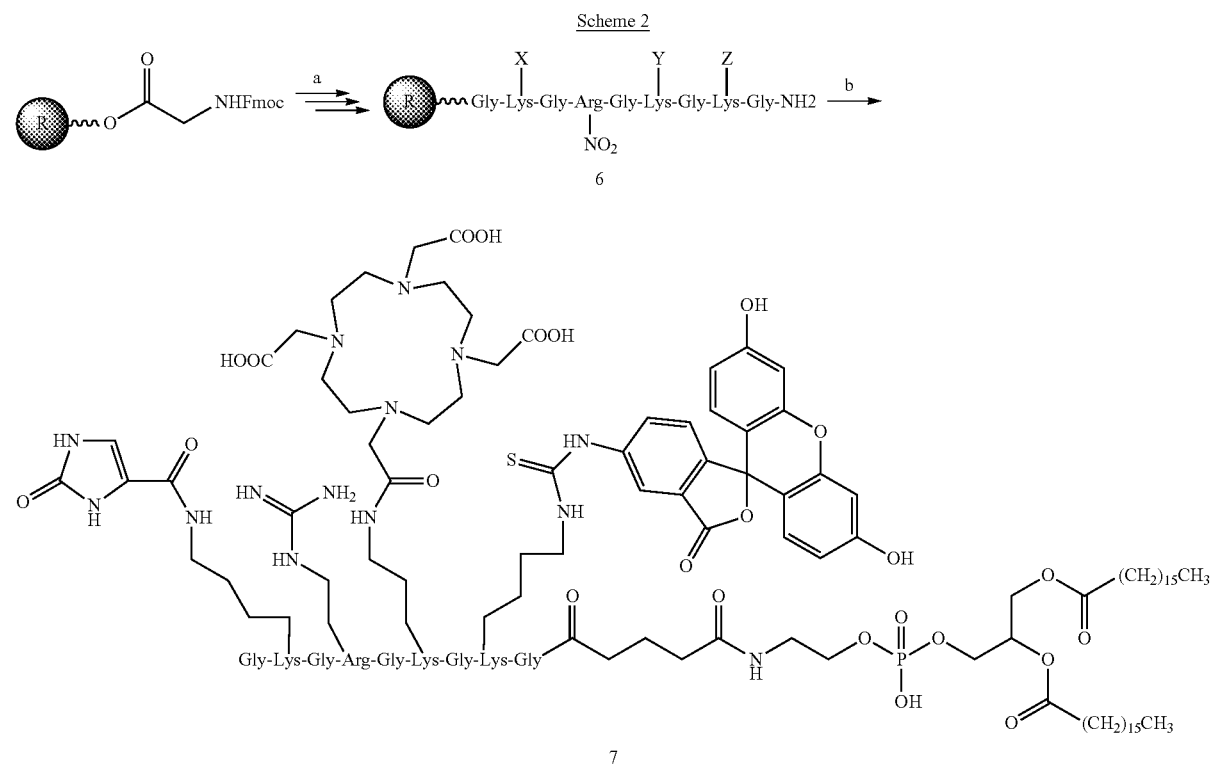
Reagents: (a) i: 20% piperine in DMF, ii: Fmoc-amino acid-OH, HBTU, HOBt, DIEA, DMF, (b) i: DSPE-glutaric NHS, TEA, DMF, ii: CF$_3$COOH, iii: H$_2$/Pd In some embodiments, the agent provides an offset from water of about 1.0 ppm to about 20 ppm, preferably from about 2 ppm to about 20 ppm, more preferably from about 4 ppm to about 20 ppm, most preferably from about 5 ppm to about 20 ppm. In some embodiments, the offset from water is at least 2.0, 2.5, 3.0, 3.5, 4.0, 4.5, 5.0, or greater from water. In particular embodiments, the offset is about 5.0 ppm.

In some embodiments, two or more different particles are prepared, each containing a different diaCEST Agent. Each specific pool of protons can be saturated selectively using radiofrequency pulses, and hence allows simultaneous monitoring of multiple particle types. Particles loaded with select types of diaCEST agents could therefore be tracked at the same time in vivo.

D. Additional Agents

The particles may contain one or more therapeutic, prophylactic, and/or diagnostic agents in addition to the diaCEST agent(s). The additional agent can be encapsulated within the particle (e.g., within the core), dispersed with the particle (e.g., dispersed within the biocompatible polymer and/or coating), and/or covalently or noncovalently associated with the surface of the particle (e.g., the polymer that forms the core and/or the coating).

Exemplary classes of agents include, but are not limited to, anti-analgesics, anti-inflammatory drugs, antipyretics, antidepressants, antiepileptics, antipsychotic agents, neuroprotective agents, anti-proliferatives, such as anti-cancer agents (e.g., taxanes, such as paclitaxel and docetaxel; cisplatin, doxorubicin, methotrexate, etc.), anti-infectious agents, such as antibacterial agents and antifungal agents, antihistamines, antimigraine drugs, antimuscarinics, anxiolytics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

The agents can be small molecules, i.e., organic, inorganic, or organometallic agents having a molecule weight less than 2000, 1500, 1200, 1000, 750, or 500 amu, biomolecules or macromolecules (e.g., having MW greater than 2000), or combinations thereof.

Examples of small molecule therapeutic agents include, but are not limited to, acyclovir, amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus and combinations thereof.

In one embodiment, the particles/liposomes contain an anti-tumor agent. Classes of antitumor agents include, but are not limited to, angiogenesis inhibitors, DNA intercalators/crosslinkers, DNA synthesis inhibitors, DNA-RNA transcription regulators, enzyme inhibitors, gene regulators, microtubule inhibitors, and other antitumor agents.

Examples of angiogenesis inhibitors include, but are not limited to, Angiostatin K1-3, DL-α-Difluoromethyl-ornithine, Endostatin, Fumagillin, Genistein, Minocycline, Staurosporine, (±)-Thalidomide, revlimid, and analogs and derivatives thereof.

Examples of DNA intercalators/cross-linkers include, but are not limited to, Bleomycin, Carboplatin, Carmustine, Chlorambucil, Cyclophosphamide, cis-Diammineplatinum (II) dichloride (Cisplatin), Melphalan, Mitoxantrone, Oxaliplatin, analogs and derivatives thereof.

Examples of DNA-RNA transcription regulators include, but are not limited to, Actinomycin D, Daunorubicin, Doxorubicin, Homoharringtonine, Idarubicin, and analogs and derivatives thereof.

Examples of enzyme inhibitors include, but are not limited to, S(+)-Camptothecin, Curcumin, (−)-Deguelin, 5,6-Dichlorobenz-imidazole 1-β-D-ribofuranoside, Etoposide, Formestane, Fostriecin, Hispidin, 2-Imino-1-imidazolidineacetic acid (Cyclocreatine), Mevinolin, Trichostatin A, Tyrphostin AG 34, Tyrphostin AG 879, and analogs and derivatives thereof.

Examples of gene regulators include, but are not limited to, 5-Aza-2'-deoxycytidine, 5-Azacytidine, Cholecalciferol (Vitamin D3), Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, Troglitazone, and analogs and derivative thereof.

Examples of microtubule inhibitors include, but are not limited to, Colchicine, Dolastatin 15, Nocodazole, Paclitaxel, docetaxel, Podophyllotoxin, Rhizoxin, Vinblastine, Vincristine, Vinorelbine (Navelbine), and analogs and derivatives thereof.

Examples of other antitumor agents include, but are not limited to, 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, Urinary trypsin inhibitor fragment (Bikunin), and analogs and derivatives thereof.

In other embodiments, the agent is a biomolecule, such as a nucleic acid. The nucleic acid can alter, correct, or replace an endogenous nucleic acid sequence The nucleic acid is used to treat cancers, correct defects in genes in other pulmonary diseases and metabolic diseases affecting lung function, genes such as those for the treatment of Parkinson's and ALS where the genes reach the brain through nasal delivery.

Gene therapy is a technique for correcting defective genes responsible for disease development. Researchers may use one of several approaches for correcting faulty genes: A normal gene may be inserted into a nonspecific location within the genome to replace a nonfunctional gene. An abnormal gene can be swapped for a normal gene through homologous recombination. The abnormal gene can be repaired through selective reverse mutation, which returns the gene to its normal function. The regulation (the degree to which a gene is turned on or off) of a particular gene can be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to use of locked nucleic acids (LNAs), unlocked nucleic acids (DNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1, 2-bensodithiol-3-one 1, 1-dioxide (BDTD). The latter methods avoid the problem of elemental sulfur's insolubility in most organic solvents and the toxicity of carbon disulfide. The TETD and BDTD methods also yield higher purity phosphorothioates.

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like. Methods for the chemical assembly of PNAs are well known.

In some embodiments, the nucleic acid includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-flouro (2'-F) pyrimidines appear to have favorable properties in vitro.

In some embodiments the nucleic acid includes one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE), 2'-0, 4'-C-methylene (LNA), 2'-O-(methoxyethyl) (2'-OME) and 2'-O—(N-(methyl)acetamido) (2'-OMA).

Methods of gene therapy typically rely on the introduction into the cell of a nucleic acid molecule that alters the genotype of the cell. Introduction of the nucleic acid molecule can correct, replace, or otherwise alters the endogenous gene via genetic recombination. Methods can include introduction of an entire replacement copy of a defective gene, a heterologous gene, or a small nucleic acid molecule such as an oligonucleotide. This approach typically requires delivery systems to introduce the replacement gene into the cell, such as genetically engineered viral vectors.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12. Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406.

E. Stability

The particles and liposomes described herein are physically and chemically stable. "Physically stable", as used herein, means that the particle size and/or polydispersity remain constant over an extended period of time.

In some embodiments, "physically stable" means the change in the average diameter of the particle is less than 10, 9, 8, 7, 6, 5, 4, 3, 2, or 1% over, 2, 4, 6, 8, 12, 16, 20, 24, 30, 36, or 48 hours. In particular embodiments, the change in the average diameter of the particles is less than 10, 9, 8, 7, 6, 5, 4, 3, or 2% after 48 hours.

In other embodiments, "physically stable" means the change in the polydispersity of the particle is less than 10, 9, 8, 7, 6, 5, 4, 3, 2, or 1% over, 2, 4, 6, 8, 12, 16, 20, 24, 30, 36, or 48 hours. In particular embodiments, the change in the polydispersity of the particles is less than 10, 9, 8, 7, 6, 5, 4, 3, 2 or 1% after 48 hours.

III. Pharmaceutical Compositions

For those embodiments where the diaCEST agent and optional additional agent(s) are encapsulated within a polymeric nanoparticle and/or associated with the surface of the nanoparticle, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of CEST agent is not limited by the methods of encapsulation. In some embodiments, the CEST agent may be encapsulated within a nanoparticle and associated with the surface of the particle. The percent loadings above also apply to additional agents encapsulated in and/or associated with the particles/liposomes, such as therapeutic agents and/or prophylactic agents.

The particles can be formulated for any route of administration. In some embodiments, the particles are formulated for enteral, parenteral, pulmonary, transmucosal, intravaginal, intracolorectal, and intracranial administration.

A. Pulmonary Formulations

Pharmaceutical formulations and methods for the pulmonary administration of active agents to patients are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

1. Dry Powder Formulations

Dry powder formulations are finely divided solid formulations containing nanoparticle carriers which are suitable for pulmonary administration. Dry powder formulations include, at a minimum, one or more nanoparticle carriers which are suitable for pulmonary administration. Such dry powder formulations can be administered via pulmonary inhalation to a patient without the benefit of any carrier, other than air or a suitable propellant.

In other embodiments, the dry powder formulations contain one or more nanoparticle gene carriers in combination with a pharmaceutically acceptable carrier. In these embodiments, the nanoparticle gene carriers and pharmaceutical carrier can be formed into nano- or microparticles for delivery to the lung.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include Exosurf—a mixture of DPPC with hexadecanol and tyloxapol added as spreading agents, Pumactant (Artificial Lung Expanding Compound or ALEC)—a mixture of DPPC and PG, KL-4—composed of DPPC, palmitoyl-oleoyl phosphatidylglycerol, and palmitic acid, combined with a 21 amino acid synthetic peptide that mimics the structural characteristics of SP-B, Venticute—DPPC, PG, palmitic acid and recombinant SP-C, Alveofact—extracted from cow lung lavage fluid, Curosurf—extracted from material derived from minced pig lung, Infasurf—extracted from calf lung lavage fluid, and Survanta—extracted from minced cow lung with additional DPPC, palmitic acid and tripalmitin.

Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more nanoparticle carriers with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

An appropriate method of particle formation can be selected based on the desired particle size, particle size distribution, and particle morphology desired for the formulation. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung. Accordingly, dry powder formulations is processed into particles having the appropriate mass median aerodynamic diameter (MMAD), tap density, and surface roughness to achieve delivery of the one or more active agents to the desired region(s) of the lung. For example, preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodynamic diameter for maximum deposition within the lungs can be calculated. See, for example, U.S. Pat. No. 7,052,678 to Vanbever, et al.

Dry powder formulations can be administered as dry powder using suitable methods known in the art. Alternatively, the dry powder formulations can be suspended in the liquid formulations described below, and administered to the lung using methods known in the art for the delivery of liquid formulations.

2. Liquid Formulations

Liquid formulations contain one or more nanoparticle carriers suspended in a liquid pharmaceutical carrier. Suitable liquid carriers include, but are not limited to water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human. Preferably, liquid formulations are mildly hypotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e. nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

In some cases, a device is used to administer the formulations to the lungs. Suitable devices include, but are not limited to, dry powder inhalers, pressurized metered dose inhalers, nebulizers, and electrohydrodynamic aerosol devices. Inhalation can occur through the nose and/or the mouth of the patient. Administration can occur by self-administration of the formulation while inhaling or by administration of the formulation via a respirator to a patient on a respirator.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

The nanoparticles may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethyl-cellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

C. Parenteral Formulations

In some embodiments, the nanoparticles are formulated for parenteral delivery, such as injection or infusion, in the form of a solution or suspension. The formulation can be administered via any route, such as, the blood stream or directly to the organ or tissue to be treated. In some embodiments, the particles/liposomes are formulated for parenteral formulation to the eye. In other formulations, the particles/liposomes are formulated for parenteral formulation to the brain (e.g., intracranial administration). The formulations can be administered intracranially via injection or implant or depot.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intracranially, intramuscularly, subcutaneously, subjunctivally, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combinations thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for ocular administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

IV. Methods of Making Nano- and Microcarriers

A. Particles

Techniques for making nanoparticles are known in the art and include, but are not limited to, solvent evaporation, solvent removal, spray drying, phase inversion, low temperature casting, and nanoprecipitation. Suitable methods of particle formulation are briefly described below. Pharmaceutically acceptable excipients, including pH modifying agents, disintegrants, preservatives, and antioxidants, can optionally be incorporated into the particles during particle formation. As described above, one or more additional active agents can also be incorporated into the nanoparticle during particle formation.

1. Solvent Evaporation

In this method, the polymeric components of the nanoparticle gene carrier are dissolved in a volatile organic solvent, such as methylene chloride. The organic solution containing the polymer-drug conjugate is then suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

2. Solvent Removal

In this method, the components of the nanoparticle gene carrier are dispersed or dissolved in a suitable solvent. This mixture is then suspended by stirring in an organic oil (such as silicon oil) to form an emulsion. Solid particles form from the emulsion, which can subsequently be isolated from the supernatant.

3. Spray Drying

In this method, the components of the nanoparticle gene carrier are dispersed or dissolved in a suitable solvent. The solution is pumped through a micronizing nozzle driven by a flow of compressed gas, and the resulting aerosol is suspended in a heated cyclone of air, allowing the solvent to evaporate from the microdroplets, forming particles.

4. Phase Inversion

In this method, the components of the nanoparticle gene carrier are dispersed or dissolved in a "good" solvent, and the solution is poured into a strong non solvent for the polymeric components of the nanoparticle gene carrier to spontaneously produce, under favorable conditions, nanoparticles.

5. Low Temperature Casting

Methods for very low temperature casting of nanoparticles are described in U.S. Pat. No. 5,019,400 to Gombotz et al. In this method, the components of the nanoparticle gene carrier are dispersed or dissolved is a solvent. The mixture is then atomized into a vessel containing a liquid non-solvent at a temperature below the freezing point of the solution which freezes the components of the nanoparticle gene carrier as tiny droplets. As the droplets and non-solvent for the components are warmed, the solvent in the droplets thaws and is extracted into the non-solvent, hardening the nanoparticles.

6. Nanoprecipitation

In this method, a solution containing one or more nucleic acids is added dropwise to a solution containing the polymeric components of the nanoparticle gene carrier. As the nucleic acids are complexed by the cationic polymers, nanoparticles precipitate from solution. The resulting nanoparticles are isolated from solution, for example by filtration or centrifugation, washed, and dried using a lyophilizer.

In a particular embodiment, the nanoparticles are prepared using an emulsification in method. In general, the particles are prepared by either o/w single emulsion or w/o/w double emulsion method as described in R. C. Mundargi et al, *J. Control. Release* 125, 193 (2008), M. Li et al., *Int. J. Pharm.* 363, 26 (2008), C. E. Astete and C. M. Sabliov, *J. Biomater. Sci. Polymer Ed.* 17, 247 (2006), and R. A. Jain, *Biomaterials,* 21, 2475 (2000). In this procedure, the polymer is dissolved in an organic solvent, such as dichloromethane, to form an oil phase. The oil phase is added to an aqueous solution of the emulsifier, typically under probe sonication for a period of time (e.g., 2 minutes) to form an emulsion. The emulsion is added to another large volume of the emulsifier with magnetic stirring to evaporate the organic solvent.

Nanoparticles are collected by centrifugation (e.g., 20,000 g for 25 mins) after filtering through a 1 μm size membrane filter and thoroughly washed with water. To prepare the nanoparticles for fluorescence microscopy, a certain amount of AF555-labeled polymers were blended before the emulsification process. In the control experiment of nanoprecipitation method, PLGA45k-PEG5k solution in acetonitrile at concentration of 25 mg/ml was slowly injected into DI water under magnetic stirring (700 rpm). After the complete removal of organic solvent, nanoparticles were collected by the same procedure as described above.

The diameter (nm), polydispersity index (PDI) and surface charge potential, mV) of nanoparticles obtained from three repeat measurements by dynamic light scattering on Zetasizer Nano ZS90 (Malvern Instruments, Southborough, Mass.). Nanoparticles were dispersed in 10 mM NaCl solution (pH 7). The morphology of the nanoparticles was characterized by transmission electron microscopy (TEM) on H7600 TEM (Hitachi, Japan).

7. Functionalization of Particle Surface

The particles described herein contain a layer or coating of a hydrophilic or amphiphilic material surrounding the core. This layer can be form at the same time as the core is formed, for example, using a block copolymer containing hydrophobic blocks and hydrophilic blocks wherein the hydrophobic blocks form the core and the hydrophilic blocks form the layer or coating that surrounds the core. The hydrophilic blocks can have covalently attached thereto one or more diaCEST agents. In other embodiments, the hydrophilic material having one or more diaCEST agents bound thereto is conjugated to the surface of finished particles. For example, PEG can be functionalized with two different functional groups at the termini: one group use to conjugate the PEG to the particle surface and the second to conjugate the diaCEST agent to the PEG.

B. Liposomes

The liposomes described herein can be prepared by a variety of techniques known in the art. The method selected is dependent on a variety of factors, such as: (1) the physicochemical characteristics of the material to be entrapped and those of the liposomal ingredients; (2) the nature of the medium in which the lipid vesicles are dispersed; (3) the effective concentration of the entrapped substance and its potential toxicity; (4) additional processes involved during application/delivery of the vesicles; (5) optimum size, polydispersity and shelf-life of the vesicles for the intended application; and (6) batch-to-batch reproducibility and possibility of large-scale production of safe and efficient liposomal products.

Formation of liposomes and nanoliposomes is not a spontaneous process. Lipid vesicles are formed when phospholipids such as lecithin are placed in water and consequently form one bilayer or a series of bilayers, each separated by water molecules, once enough energy is supplied. Liposomes can be created by sonicating phosphatidylcholine rich phospholipids in water. Low shear rates create multilamellar liposomes, which have many layers like an onion.

Continued high-shear sonication tends to form smaller unilamellar liposomes. In this technique, the liposome contents are the same as the contents of the aqueous phase. Sonication is generally considered a "gross" method of preparation as it can damage the structure of the drug to be encapsulated. Newer methods such as extrusion and Mozafari method are employed to produce materials for animal (e.g., human) use.

In some embodiments, liposomal particles are prepared using a conventional thin film hydration and extrusion method. The lipid, PEG-conjugated lipid, and stabilizer, if present, are dissolved in an organic solvent (e.g., chloroform) at pre-determined molar ratios. A small proportion of a labeled-lipid, such as rhodamine labeled PE (Rho-PE), can be added to the mixture to enable visualization of the liposomal particles via fluorescence microscopy. The mixture is placed in a rotavap with reduced atmosphere pressure to evaporate the organic solvent. The resulting lipid film is hydrated, such as with phosphate buffered saline (PBS), while agitated using a water bath sonicator to form multilamellar vehicles (MLV). The suspension is subsequently extruded through polycarbonate filters with pore sizes of 400 nm and 200 nm to generate unilamellar vehicles (LUV, i.e., liposomes with single bilayer membrane).

V. Methods of Using Nanoparticles

The particles described herein can be used for a variety of applications including tracking release of active agents encapsulated in the particles in order to evaluate pharmacological outcomes in patients. In one embodiment, the particles are images and tracked using chemical exchange saturation transfer (CEST). Particles having different therapeutic agents and different CEST agents can be monitored simultaneously. The particles described herein contain CEST agents not conventional paramagnetic or superparamagnetic metal-based agent, which avoids the toxicity issues associated with these agents.

A. Chemical Exchange Saturation Transfer (CEST)

Chemical exchange saturation transfer (CEST) is a magnetic resonance imaging (MRI) contrast enhancement technique that enables indirect detection of contrast agents with exchangeable protons. Contrast agents with exchangeable protons including, but not limited to, L-arginine, barbituric acid, many analogs of barbituric acid with replacement of the hydrogen at the 5 position by an organic group, glycogen, glucose, myoinositol, glutamate, creatine and many polycationic peptides have been identified as potential in vivo CEST agents. Exogenous agents, such as diagnostic agents or contrast agents, can also be used for in vivo imaging. CEST technology has a number of indispensable features, such as the possibility of simultaneous detection of multiple 'colors' of agents and of changes in their environment (e.g. pH, metabolites, etc.) through MR contrast.

CEST exploits the ability of Nuclear Magnetic Resonance (NMR) to resolve different signals arising from protons on different molecules. By selectively saturating a particular proton signal (associated with a particular molecule or CEST agent) that is in exchange with surrounding water molecules, the MRI signal from the surrounding bulk water molecules is also attenuated. Images obtained with and without the RF saturating pulse reveal the location of the CEST agent. The chemical exchange must be in the intermediate regime where exchange is fast enough to efficiently saturate the bulk water signal but slow enough that there is a chemical shift difference between the exchangeable proton and the water proton resonances. The magnitude of the CEST effect therefore depends on both the exchange rate and the number of exchangeable protons.

CEST has three main advantages over traditional molecular imaging techniques: (1) the image contrast is controlled with radio-frequency (RF) pulses and can be turned on/off at will; (2) The molecules of interest, in some cases, can be directly detected, eliminating the need for contrast agent to be delivered to, and to specifically react with, the molecule of interest; (3) A variant of the CEST technique, known as PARACEST, may be much more sensitive than traditional molecular imaging techniques and should be able to detect nanomolar concentrations. PARACEST typically relies on water exchange between the bulk water and water bound to paramagnetic Lanthanide complexes. Saturation of the Lanthanide ion bound water resonance leads to attenuation of the bulk water signal via water exchange. The large paramagnetic chemical shift of the bound water molecules allows them to tolerate much faster exchange rates with the bulk water while still while still remaining in the intermediate exchange regime, thereby providing much more efficient saturation of the bulk water signal and much greater CEST sensitivity.

1. Delivery of Chemotherapeutic Agents

Nanosized drug delivery particles possess an innate ability to target tumors via leaky tumor vasculature. Once at the tumor, the particles release the drug payload in a steady fashion over a prolonged period of time, which reduces the risk of adverse reactions and greatly improves drug efficacy. However, when drug-loaded nanoparticles are administered to a patient, there is currently no way to confirm that the particles were administered properly and/or reached their target (tumor), or determine how long they persist in the tumor (which can guide dosing regimens).

CEST can be used to monitor drug delivery at a desired site from the particles/liposomes described herein. For example, CEST can be used to monitor drug delivery from particles/liposomes for local treatment of tumors by coencapsulating diamagnetic CEST contrast agents and drugs within the particles/liposomes described herein or conjugating the CEST agent to the particles.

The particles/liposomes described herein exhibit good temporal and spatial resolution for in vivo imaging using diaCEST. The nanoparticles produce artificial "color" MR images that allow discrimination between multiple agents, a significant advantage in monitoring combination therapies, such as but not limited to, combination chemotherapy.

EXAMPLES

Example 1. Preparation of DiaCEST Liposomes

Drug-containing liposomes were prepared with the poly (ethylene) glycol (PEG) concentration varied systematically using the thin film hydration method. 25 mg of lipid dissolved in chloroform was dried, with the resultant thin film hydrated using 1 ml barbituric acid (BA) to form multilamellar vesicles. The mixture was then annealed at 55-65° C., sonicated, and subsequently extruded through stacked polycarbonate filters. Doxorubincin (DOX) was then loaded into the liposomes remotely.

Example 2. Preparation of DiaCEST Polymeric Particles

Polymeric particle preparation: The peptide contrast agent, propargylglycine-W-(DYD)6-$NH_2$, was synthesized on a microwave-assisted peptide synthesizer Libertyl (CEM, USA). The CEST nanoparticles were then prepared by standard coupling chemistry. $NH_2PEG-N_3$ was coupled to carboxylates on the surface of polystyrene (PS) particles in the presence of EDC and NHS in 200 mM sodium borate buffer pH 7.8 at RT. Propargylglycine-W-(DYD)6-$NH_2$ peptide was coupled with PS-PEG-$N_3$ in the presence of catalytic amount of CuAcAc, TBTA, and excess ascorbic acid in sodium phosphate buffer pH 7, under nitrogen, using click chemistry. Biodegradable CEST nanoparticles based on the polymer of poly(lactic-co-glycolic) acid-co-PEG (PLGA-PEG) were synthesized using a similar procedure and formulated using a oil-in-water emulsion method.

Example 3. Animal Preparation

Five million CT26 cells were injected subcutaneously into the right flank of a mouse and allowed to grow for ~10 days prior to MRI.

CEST Imaging

Mice were anesthetized using isoflurane, positioned in a 11.7 T horizontal bore Bruker Biospec scanner, and imaged before and 24 h after intravenous administration of 100 ul of DOX/BA PEGylated liposomes. CEST images were acquired through collection of two sets of saturation images, a water saturation shift referencing (WASSR) set for B0 mapping and a CEST data set for characterizing contrast. For the WASSR images, the saturation parameters were tsat=500 ms, B1=0.5 uT, TR=1.5 sec with saturation offset incremented from −1 to +1 ppm with respect to water in 0.1 ppm steps.

For the CEST images, tsat=3 sec, B1=4.7 uT, TR=Ssec, with offset incremented from −6 to +6 ppm (0.3 ppm steps) with a fat suppression pulse. The acquisition parameters were TR=5.0 sec, effective TE=21.6 ms, RARE factor=8. The CEST images were acquired before and 24 h after the liposome administration.

Data Analysis

MR images were processed using custom-written Matlab scripts with the CEST contrast quantified by calculating the asymmetry in the magnetization transfer ration ($MTR_{asym}$) using $MTR_{asym}=(S^{-\Delta\omega)}-S^{\Delta\omega})/S_o$ for NH protons at $\Delta\omega=5$ ppm.

Results and Discussion

Figure 4A:
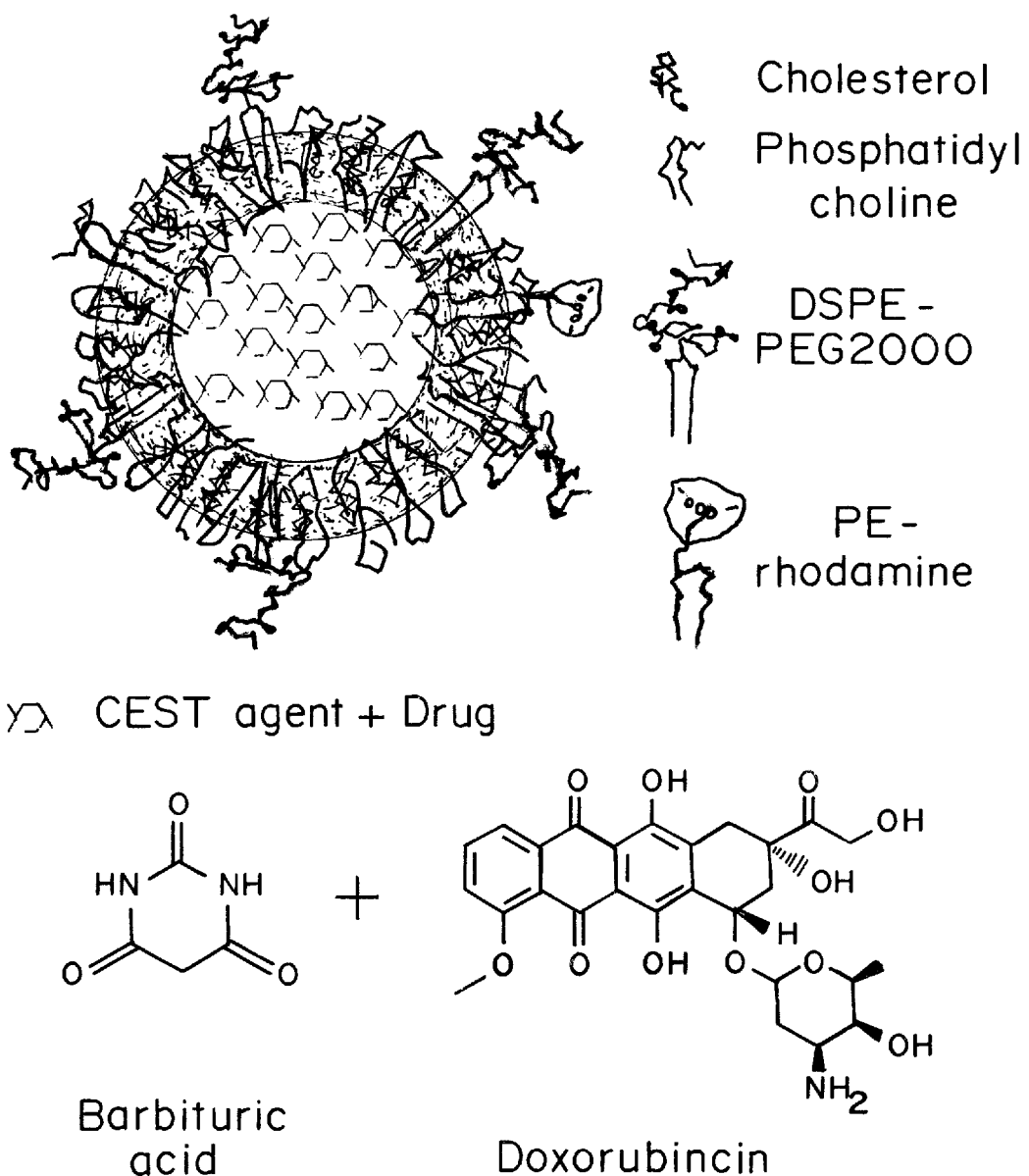
FIG. 4a is a schematic of the doxorubicin/barbituric acid liposomes.
Figure 4B:
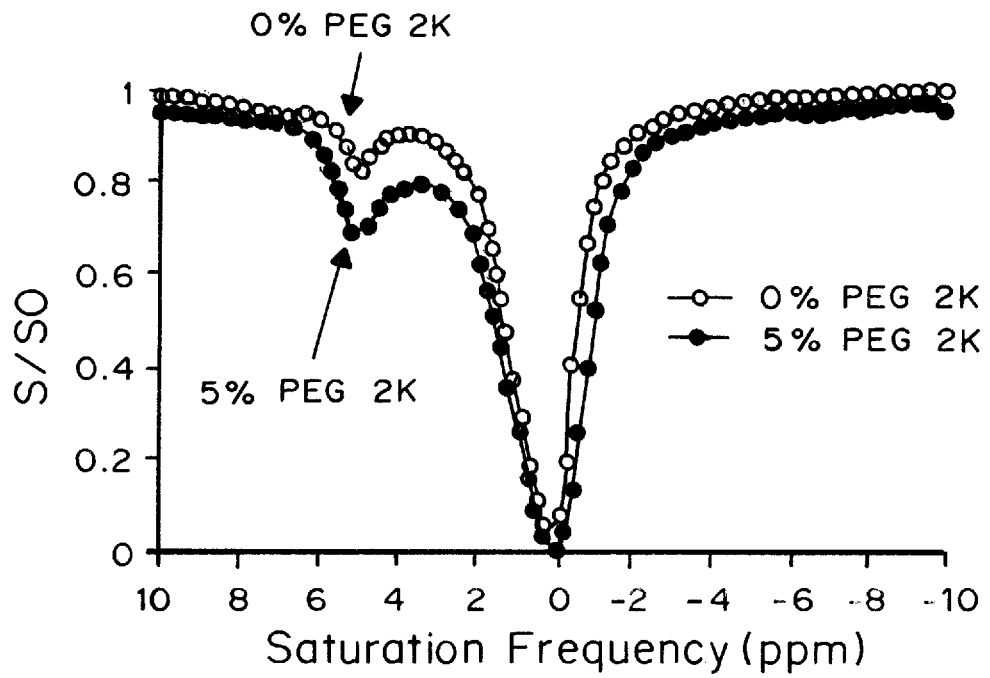
FIG. 4b is a graph showing the Z-spectra for two liposome formulations containing 0% and 5% PEG 2K.
Figure 4C:
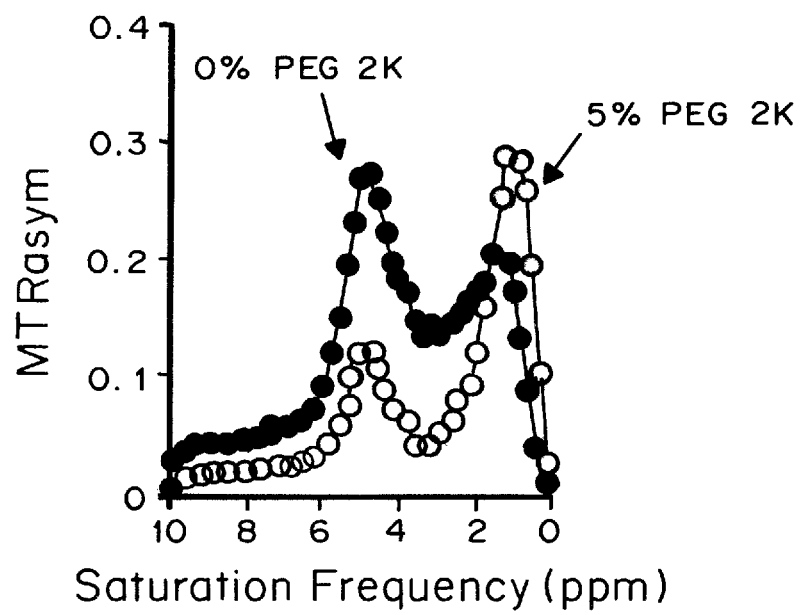
FIG. 4c is a graph showing the $MTR_{asym}$ for two liposome formulations containing 0% and 5% PEG 2K.

The liposomes were loaded with BA (CEST imaging agent) and DOX (chemotherapeutic) as shown in FIG. 4(a). The in vitro CEST contrast for these liposomes with 0% and 5% PEG was 24% and 13%, respectively at 5 ppm as shown in FIG. 4(b). In order to determine if these formulations would be stable within an imaging window up to 24 h, the CEST contrast among different formulation at 24 h after dialysis was compared. The formulation with the highest contrast had about 20% BA retained in the liposomes 24 h after dialysis and was selected for in vivo study. In addition, the CEST liposomes were tested in vivo to determine their sensitivity on mice bearing the CT26 colon carcinoma. Images were taken before and 24 h after i.v. injection of DOX/BA liposomes acquiring single slice CEST images of the colon tumors. The CEST images were acquired using WASSR to compensate for B) inhomogeneity artifacts across the slice and using a CNR filter to remove artifacts similar to the methods described previously which were suitable for in vivo multi-color imaging. The CEST liposomes could be detected readily after administration and their distribution can be assessed after 24 h of administration.

Figure 5A:
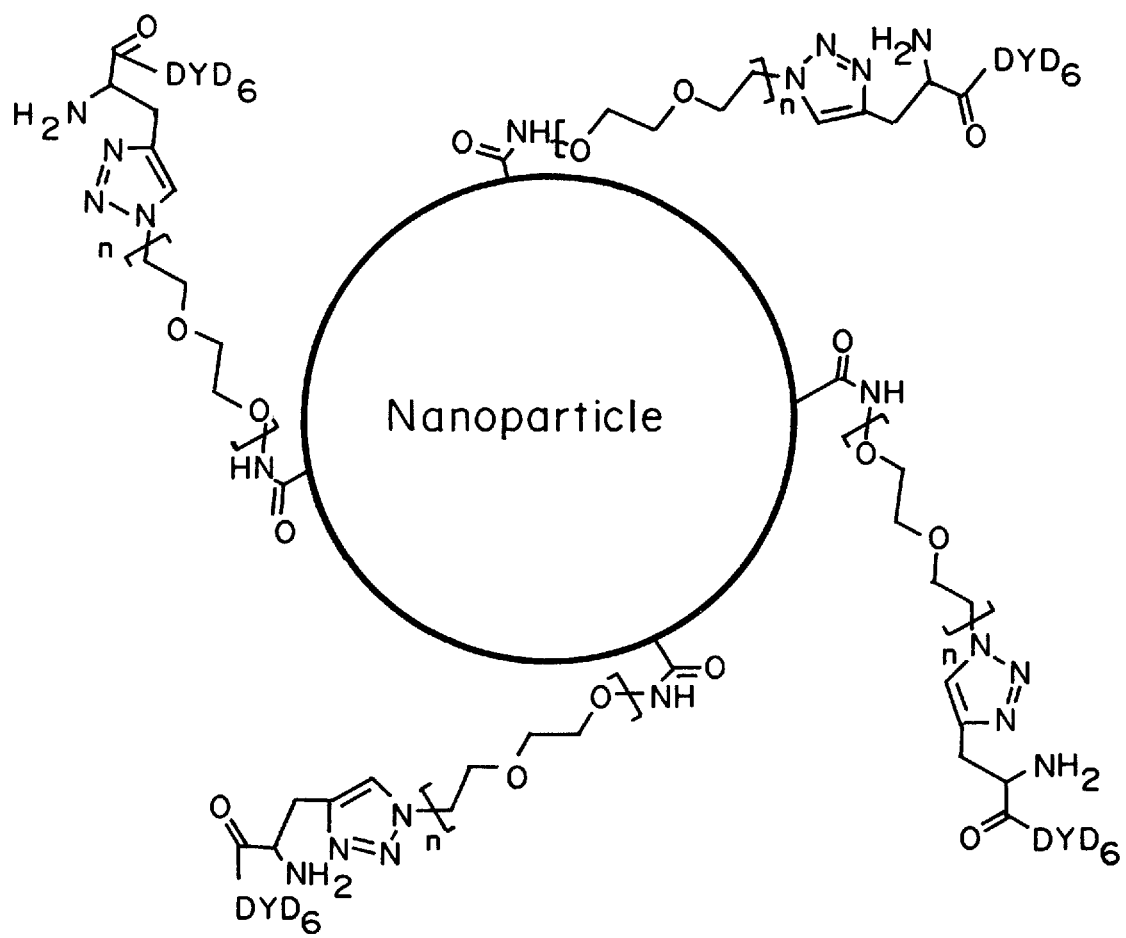
FIG. 5a is a schematic of the polymeric CEST nanoparticles.
Figure 5B:
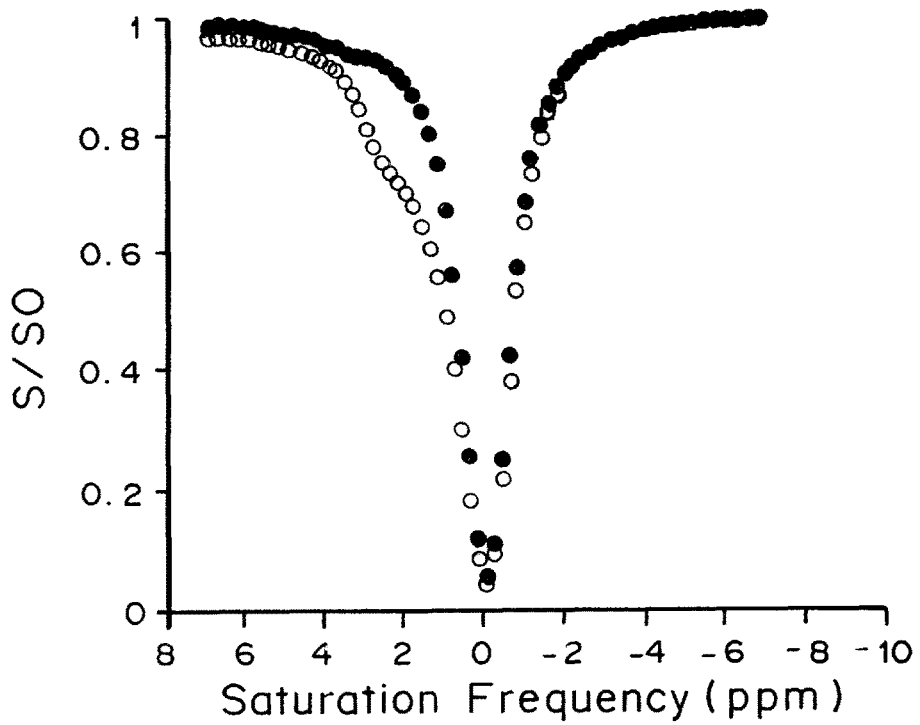
FIG. 5b is a graph showing the Z-spectra for two nanoparticle formulations with a PEG 5.6K spacer and a PEG 0.6K spacer.
Figure 5C:
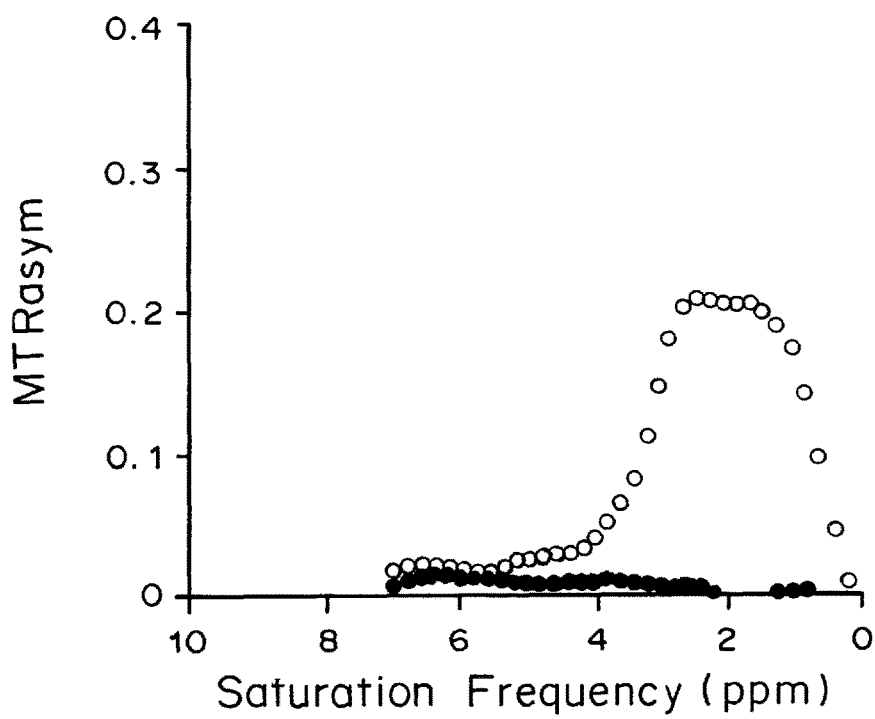
FIG. 5c is a graph showing the MTRasym for two liposome formulations containing PEG 5.6K spacer and a PEG 0.6K spacer.

The nanoparticles are suitable for tumor delivery. As the interior of the nanoparticles has reduced water accessibility compared to liposomes, the CEST agent was conjugated to the surface of the particle as shown in FIGS. 5(a) through 5(c). Two versions were prepared, one with a short (0.6 kDa) and a second with a longer PEG spacer (5.6 kDa). As shown in FIGS. 5(a) through 5(c), the longer PEG spacer was necessary to retain the peptide's CEST contrast after conjugation, presumably to provide sufficient motion to produce a sharp exchangeable proton line shape. The DYD peptide provides contrast centered around 2.5 ppm from water, which should allow discrimination with the BA liposomes through multi-color CEST imaging.

We claim:

1. A particle comprising
a biocompatible, hydrophobic polymeric core,
having covalently bound to the core surface altering polymeric agents comprising a polyalkylene oxide, the polymeric agents having a molecular weight between about 1,000 Daltons and about 10,000 Daltons,
wherein the density of the surface altering agent is between about 0.1 and about 1000 chains/blocks/moieties per 100 nm$^2$, and
a plurality of diamagnetic chemical exchange saturation transfer (diaCEST) agents covalently coupled to the surface altering polymeric agents,
wherein the diaCEST agent is selected from the group consisting of L-arginine; barbituric acid; substituted barbituric acid with F, COOH, carbonyl, phospholipid at one or more ring atoms or protons attached thereto; salicylic acid; 4-amino-salicylic acid; imidazole; substituted imidazole with Br, COOH, carbonyl, phospholipid, peptide at one or more ring atoms or protons attached thereto, peptides rich in backbone NH, guanidyl NH$_2$, and/or OH protons; and combinations thereof,
wherein the diaCEST agents are presented on the surface of the particles and the surface altering polymeric agents are of sufficient length to exhibit good temporal and spatial resolution of the diaCEST agent for in vivo imaging in the absence of a metal-based contrast agent.

2. The particle of claim 1, wherein the core comprises a polymer selected from the group consisting of polystyrenes; poly(hydroxy acids); poly(lactic acid); poly(glycolic acid); poly(lactic acid-co-glycolic acid); polyanhydrides; polyorthoesters; polyamides; polycarbonates; polyalkylenes; polyalkylene terephthalates; polyvinyl ethers; polyvinyl esters; polyvinyl halides; polysiloxanes; polyurethanes; copolymers of polyurethanes; alkyl cellulose; cellulose esters;

polycarbonate-urethane polymers; silicone-urethane polymers; epoxy polymers; polycarbonate urethane; silicone urethane; polyvinylpyridine copolymers; polyether sulfones; polydimethyl siloxane; polyesters; polyureas; polyimides; polysulfones; polyacetylenes; and combinations, copolymers and/or mixtures thereof.

3. The particle of claim 1, wherein the polyalkylene oxide is polyethylene glycol.

4. The particle of claim 1 wherein the diaCEST agent is L-arginine.

5. The particle of claim 1, wherein the diaCEST agent is barbituric acid.

6. The particle of claim 1, wherein the diaCEST agent is propargylglycine-W-(DYD)$_6$.

7. The particle of claim 1 wherein the particle further contains one or more therapeutic and/or prophylactic agents.

8. The particle of claim 7, wherein the one or more therapeutic and/or diagnostic agents are selected from the group consisting of, anti-analgesics, anti-inflammatory drugs, antipyretics, antidepressants, antiepileptics, antipsychotic agents, neuroprotective agents, anti-proliferatives, antihistamines, antimigraine drugs, antimuscarinics, anxiolytics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics, anti-narcoleptics, nutraceuticals, and combinations thereof.

9. The particle of claim 8, wherein the therapeutic and/or diagnostic agent is a chemotherapeutic agent.

10. The particle of claim 9, wherein the chemotherapeutic agent is a taxane.

11. A population of particles comprising two or more particles of claim 1,
wherein the particles contain different diaCEST agents and/or different therapeutic or prophylactic agents.

12. A pharmaceutical composition comprising an effective amount for imaging of
particles of claim 1,
wherein the diaCEST agents are presented on the surface of the particles and the surface altering polymeric agents are of sufficient length to exhibit good temporal and spatial resolution of the diaCEST agent for in vivo imaging in the absence of a metal-based contrast agent, or
the population of these particles comprising two or more of these particles containing different diaCEST agents and/or different therapeutic or prophylactic agents,
in one or more pharmaceutically acceptable carriers.

13. The composition of claim 12 in the form of a solution.

14. The composition of claim 12 in the form of a suspension.

15. A method for CEST imaging in vivo comprising administering a pharmaceutical composition comprising an effective amount for imaging of
particles of claim 1,
wherein the diaCEST agents are presented on the surface of the particles and the surface altering polymeric agents are of sufficient length to exhibit good temporal and spatial resolution of the diaCEST agent for in vivo imaging in the absence of a metal-based contrast agent, or
the population of these particles comprising two or more of these particles containing different diaCEST agents and/or different therapeutic or prophylactic agents,
in one or more pharmaceutically acceptable carriers, and imaging the particles using magnetic resonance imaging.

16. The method of claim 15, wherein the particles are administered parenterally.

17. The method of claim 15, wherein the particles are administered by injection.

18. The method of claim 15 comprising administering the population of particles of claim 11.

19. The method of claim 18, wherein the population contains two or more different types of particles containing different diaCEST agents and different therapeutic or prophylactic agents and wherein each specific pool of protons on the different diaCEST agents is saturated selectively using radiofrequency pulses to simultaneously image the different types of particles.

20. The particle of claim 3, wherein the polyethylene glycol has a molecular weight from about 1,000 Daltons to about 8,000 Daltons.

21. The particle of claim 3, wherein the polyethylene glycol has a molecular weight from about 1,000 Daltons to about 6,000 Daltons.

22. The particle of claim 3, wherein the polyethylene glycol has a molecular weight from about 4,000 Daltons to about 6,000 Daltons.

23. The particle of claim 2, wherein the polyester is a poly(hydroxy acid), copolymer, or mixture thereof.

24. The particle of claim 23, wherein the poly(hydroxy acid) is selected from the group consisting of poly(lactic acid) poly(glycolic acid), poly(lactic acid-co-glycolic acid), and a combination thereof.

25. The particle of claim 23, wherein the poly(hydroxy acid) or copolymer thereof is selected from the group consisting of poly(lactide-co-caprolactone), copolymer of poly(lactide-co-caprolactone), or mixtures of poly(lactide-co-caprolactone).

26. The particle of claim 2, wherein the polyalkylene is selected from the group consisting of polyethylenes, polypropylenes, and a combination thereof.

27. The particle of claim 1, wherein the polyalkylene oxide is polyoxypropylene (PPO) or copolymers thereof.

* * * * *

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Lys Ser Ser Ser
1

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Thr Thr Thr Thr Thr Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Thr Thr Thr Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Lys Gly Gly Gly
1

```
<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Asp Ser Ser Ser Ser Ser
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Arg Thr Thr Thr
1

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 7

Asp Thr Thr Thr Thr Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 8

Glu Thr Thr Thr Thr Thr
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 9

Glu Thr Thr Thr
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 10

Asp Thr Thr Thr
1
```

```
<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 11

Asp Ser Ser Ser
1

<210> SEQ ID NO 12
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: G = Propargylglycine
<220> FEATURE:
<221> NAME/KEY: MISC_FEATURE
<222> LOCATION: (20)..(20)
<223> OTHER INFORMATION: NH2- modification

<400> SEQUENCE: 12

Gly Trp Asp Tyr Asp Asp Tyr Asp Asp Tyr Asp Asp Tyr Asp Asp Tyr
1               5                   10                  15

Asp Asp Tyr Asp
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: G = Propargylglycine

<400> SEQUENCE: 13

Gly Trp Asp Tyr Asp Asp Tyr Asp Asp Tyr Asp Asp Tyr Asp Asp Tyr
1               5                   10                  15

Asp Asp Tyr Asp
            20
```